US010017528B2

(12) United States Patent
Mazaheripour et al.

(10) Patent No.: US 10,017,528 B2
(45) Date of Patent: Jul. 10, 2018

(54) CONTROLLED SYNTHESIS OF POLYMERIC PERYLENE DIIMIDE AND APPLICATIONS THEREOF

(71) Applicant: The Regents of the University of California, Oakland, CA (US)

(72) Inventors: Amir Mazaheripour, Irvine, CA (US); Anthony Burke, Anaheim, CA (US); Alon Gorodetsky, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/707,851

(22) Filed: Sep. 18, 2017

(65) Prior Publication Data

US 2018/0099986 A1 Apr. 12, 2018

Related U.S. Application Data

(60) Provisional application No. 62/396,020, filed on Sep. 16, 2016.

(51) Int. Cl.
 *C07F 9/06* (2006.01)
 *H01L 51/50* (2006.01)
 *C07F 9/6561* (2006.01)
(52) U.S. Cl.
 CPC .................. *C07F 9/6561* (2013.01)
(58) Field of Classification Search
 CPC ... C07F 9/06; C07F 9/59; H01L 51/50; H01L 51/00
 USPC .................... 546/23; 313/504, 498
 See application file for complete search history.

(56) References Cited

PUBLICATIONS

Rivnay, et al., "Quantitative Determination of Organic Semiconductor Microstructure from the Molecular to Device Scale", Chem. Rev., 2012, vol. 112, dx.doi.org/10.1021/cr3001109, pp. 5488-5519.
Robinson, et al., "Submicrosecond Electron Transfer to Monolayer-Bound Redox Species on Gold Electrodes at Large Overpotentials", J. Phys. Chem. B, 2002, vol. 106, No. 41, pp. 10706-10713.
Ruben, et al., "Visions for a molecular future", Nature Nanotechnology, Jun. 2013, vol. 8, pp. 385-389.
Samuel, et al., "NEXAFS characterization of DNA components and molecular-orientation of surface-bound DNA oligomers", Journal of Electron Spectroscopy and Related Phenomena, vol. 152, 2006, pp. 134-142.
Schiros et al., "Donor-Acceptor Shape Matching Drives Performance in Photovoltaics", Advanced Energy Materials, vol. 3, Issue 7, Jul. 2013, published online Mar. 12, 2013, pp. 894-902.
Schnadt, et al., "Comparison of the size of excitonic effects in molecular π systems as measured by core and valence spectroscopies", Chemical Physics, vol. 312, 2005, pp. 39-45.
Schubert et al., "Molecular wires—impact of π-conjugation and implementation of molecular bottleneck", Chemical Society Reviews, vol. 44, Issue 4, 2015, published online Oct. 15, 2014, pp. 988-998.
Sedghi et al., "Comparison of the Conductance of Three Types of Porphyrin-Based Molecular Wires: β,meso,β-Fused Tapes, meso-Butadiyne-Linked and Twisted meso-meso Linked Oligomers", Advanced Materials, vol. 24, Issue 5, Feb. 2, 2012, pp. 653-657.
Sedghi et al., "Long-range electron tunnelling in oligo-porphyrin molecular wires", Nature Nanotechnology, vol. 6, Jul. 31, 2011, pp. 517-523.
Sikes et al., "Rapid Electron Tunneling Through Oligophenylenevinylene Bridges", Science, vol. 291, Issue 5508, Feb. 23, 2001, pp. 1519-1523.
Sirringhaus, "25th Anniversary Article: Organic Field-Effect Transistors: The Path Beyond Amorphous Silicon", Advanced Materials, 2014, vol. 26, pp. 1319-1335.
Skourtis, Spiros S. "Review probing protein electron transfer mechanisms from the molecular to the cellular length scales", Peptide Science, vol. 100, Issue 1, Jan. 19, 2013, pp. 82-92.
Slinker et al., "DNA charge transport over 34 nm", Nature Chemistry, vol. 3, Mar. 2011, published online Jan. 30, 2011, pp. 228-233.
Smalley, et al., "Heterogeneous Electron-Transfer Kinetics for Ruthenium and Ferrocene Redox Moieties through Alkanethiol Monolayers on Gold", J. Am. Chem. Soc., 2003, vol. 125, No. 7, pp. 2004-2013.
Song et al., "Single Molecule Electronic Devices", Advanced Materials, vol. 23, Issue 14, Apr. 12, 2011, pp. 1583-1608.
Stöhr, Joachim "NEXAFS Spectroscopy", Springer-Verlag, Berlin/Heidelberg, Germany, 1992, 418 pgs. (presented in two parts).
Sun, et al., "Water-soluble perylenediimides: design concepts and biological applications", Chem. Soc. Rev., 2016, vol. 45, pp. 1513-1528.
Tan, et al., "Charge transport in DNA nanowires connected to carbon nanotubes", Physical Review B, 2015, vol. 92, pp. 075429-1-075429-7.
Tang, et al., "Functional DNA switches: rational design and electrochemical signaling", Chem. Soc. Rev., 2014, vol. 43, pp. 518-529.
Tao, "Electron transport in molecular junctions", Nature Nanotechnology, vol. 1, Dec. 1, 2006, pp. 173-181.

(Continued)

*Primary Examiner* — Charanjit Aulakh
(74) *Attorney, Agent, or Firm* — KPPB LLP

(57) ABSTRACT

Perylene diimide phosphoramidite derivatives and methods for polymerization of perylene diimide phosphoramidite derivatives and applications thereof are provided. Compounds comprise at least an electronically active base surrogate and may also include a solubilizing functionality. The base surrogate may be comprised of an electrochemically active perylene diimide (PDI) molecule, the solubility chain may comprise a PEG functionality, and the PDI may further comprise a phosphoramidite functionality as an imide substituent. The phosphoramidite functionality may be used as a chemical coupling handle for use with established nucleic acid synthesis protocols and/or automated synthesis. One or more aromatic core functionalizations may be incorporated into the PDI molecules to allow for tuning the molecule's electronic and optical properties. One or more functional terminal groups may be incorporated into the PDI molecules, such as, for example terminal thiols for attachment to gold substrates and terminal ferrocenes for electrochemical measurements, among others.

34 Claims, 32 Drawing Sheets

(56) References Cited

PUBLICATIONS

Tao, et al., "Understanding Odd-Even Effects in Organic Self-Assembled Monolayers", Chem. Rev., 2007, vol. 107, 10.1021/cr050258d, pp. 1408-1453.
Teo, et al., "DNA-Multichromophore Systems", Chem. Rev., 2012, vol. 112, pp. 4221-4245.
Tessler, et al., "Charge Transport in Disordered Organic Materials and Its Relevance to Thin-Film Devices: A Tutorial Review", Adv. Mater., 2009, vol. 21, pp. 2741-2761.
Thorsmølle, et al., "Morphology Effectively Controls Singlet-Triplet Exciton Relaxation and Charge Transport in Organic Semiconductors", Physical Review Letters, 2009, vol. 102, pp. 017401-1-017401-4.
Thuo, et al., "Odd-Even Effects in Charge Transport across Self-Assembled Monolayers", J. Am. Chem. Soc., 2011, vol. 133, pp. 2962-2975.
Varghese et al., "DNA as a supramolecular framework for the helical arrangements of chromophores: towards photoactive DNA-based nanomaterials", Chemical Communications, Issue 19, Apr. 6, 2009, pp. 2615-2624.
Vilmercati et al., "Heterostructured organic interfaces probed by resonant photoemission", Surface Science, vol. 603, Issues 10-12, Jun. 1, 2009, pp. 1542-1556.
Virkar, et al., "Organic Semiconductor Growth and Morphology Considerations for Organic Thin-Film Transistors", Adv. Mater., 2010, vol. 22, pp. 3857-3875.
Vura-Weis, et al., "Geometry and Electronic Coupling in Perylenediimide Stacks: Mapping Structure—Charge Transport Relationships", J. Am. Chem. Soc., 2010, vol. 132, pp. 1738-1739.
Wagenknecht, "Synthetic Oligonucleotide Modifications for the Investigation of Charge Transfer and Migration Processes in DNA", Current Organic Chemistry, vol. 8, No. 3, Feb. 2004, pp. 251-266.
Wagner et al., "Perylene-3,4:9,10-tetracarboxylic Acid Bisimide Dye as an Artificial DNA Base Surrogate", Organic Letters, vol. 8, No. 19, Aug. 18, 2006, pp. 4191-4194.
Waldrop, "The chips are down for Moore's law", Nature, vol. 530, Issue 7589, Feb. 11, 2016, pp. 144-147.
Wang, et al., "Configuration-Dependent Interface Charge Transfer at a Molecule-Metal Junction", J. Am. Chem. Soc., 2006, vol. 128, pp. 8003-8007.
Wang, et al., "Resonant photoemission study of single-strand deoxyribonucleic acid", Applied Physics Letters, vol. 89, 2006, 3 pgs.
Ward, et al., "The interplay of thermally activated delayed fluorescence (TADF) and room temperature organic phosphorescence in sterically-constrained donor-acceptor charge-transfer molecules", Chem. Commun., 2016, vol. 52, pp. 2612-2615.
Wardrip, et al., "Length-Independent Charge Transport in Chimeric Molecular Wires", Angew. Chem. Int. Ed., 2016, vol. 55, DOI:10.1002/anie.201605411, pp. 14267-14271.
Wasielewski, "Photoinduced Electron Transfer in Supramolecular Systems for Artificial Photosynthesis", Chem. Rev., 1992, vol. 92, pp. 435-461.
Weber, et al., "Long-Range Electronic Coupling between Ferrocene and Gold in Alkanethiolate-based Monolayers on Electrodes", J. Phys. Chem. B, 1997, vol. 101, No. 41, pp. 8286-8291.
Weiss et al., "Molecules as wires: molecule-assisted movement of charge and energy", Topics in Current Chemistry, vol. 257, Jul. 6, 2005, pp. 103-133.
Willenbockel, et al., "The interplay between interface structure, energy level alignment and chemical bonding strength at organic—metal interfaces", Phys. Chem. Chem. Phys., 2015, vol. 17, pp. 1530-1548.
Wilson et al., "Electron Hopping among Cofacially Stacked Perylenediimides Assembled by Using DNA Hairpins", Angewandte Chemie International Edition, vol. 49, Issue 13, Mar. 22, 2010, pp. 2385-2388.
Winters, et al., "Probing the Efficiency of Electron Transfer through Porphyrin-Based Molecular Wires", J. Am. Chem. Soc., 2007, vol. 129, pp. 4291-4297.
Wirges et al., "Controlled Nucleation of DNA Metallization", Angewandte Chemie International Edition, vol. 48, Issue 1, Dec. 22, 2008, pp. 219-223.
Wohlgamuth et al., "Electrochemistry of DNA Monolayers Modified With a Perylenediimide Base Surrogate", The Journal of Physical Chemistry C, vol. 118, Issue 50, Aug. 12, 2014, pp. 29084-29090.
Würthner, "Perylene bisimide dyes as versatile building blocks for functional supramolecular architectures", Chemical Communications, Issue 14, May 12, 2004, pp. 1564-1579.
Würthner, et al., "Perylene Bisimide Dye Assemblies as Archetype Functional Supramolecular Materials", Chem. Rev., 2016, vol. 116, pp. 962-1052.
Xiang et al., "Intermediate tunnelling-hopping regime in DNA charge transport", Nature Chemistry, vol. 7, Mar. 2015, published online Feb. 20, 2015, pp. 221-226.
Xiao, et al., "Recent Progresses on Materials for Electrophosphorescent Organic Light-Emitting Devices", Advanced Materials, 2011, vol. 23, pp. 926-952.
Xu, et al., "Recent advances in flexible organic light-emitting diodes", J. Mater. Chem. C, 2016, vol. 4, pp. 9116-9142.
Yanai, et al., "A new hybrid exchange-correlation functional using the Coulomb-attenuating method (CAM-B3LYP)", Chemical Physics Letters, vol. 393, 2004, pp. 51-57.
Yokoyama, et al., "Molecular orientation in small-molecule organic light-emitting diodes", J. Mater. Chem., 2011, vol. 21, pp. 19187-19202.
Yoo, et al., "Electrical Conduction through Poly(dA)-Poly(dT) and Poly(dG)-Poly(dC) DNA Molecules", Physical Review Letters, vol. 87, No. 19, Nov. 5, 2001, pp. 198102-1-198102-4.
Yu, et al., "Crystallization-Induced Charge-Transfer Change in TiOPc Thin Films Revealed by Resonant Photoemission Spectroscopy", J. Phys. Chem. C, 2011, vol. 115, pp. 14969-14977.
Zeidan et al., "Charge-Transfer and Spin Dynamics in DNA Hairpin Conjugates with Perylenediimide as a Base-Pair Surrogate", Journal of the American Chemical Society, vol. 130, Issue 42, Sep. 24, 2008, pp. 13945-13955.
Zhang, et al., "Energy level alignment and morphology of interfaces between molecular and polymeric organic semiconductors", Organic Electronics, vol. 8, 2007, pp. 606-614.
Zharnikov, "Probing charge transfer dynamics in self-assembled monolayers bycore hole clock approach", Journal of Electron Spectroscopy and Related Phenomena, vol. 200, 2015, pp. 160-173.
Zhu, "Charge Transport at Metal-Molecule Interfaces: A Spectroscopic View", J. Phys. Chem. B, 2004, vol. 108, pp. 8778-8793.
"Best Research-Cell Efficiencies", National Renewable Energy Laboratory, 2015, http://www.nrel.gov/ncpv/images/efficiency_chart.jpg, 1 pg.
Anne, et al., "Dynamics of Electron Transport by Elastic Bending of Short DNA Duplexes. Experimental Study and Quantitative Modeling of the Cyclic Voltammetric Behavior of 3'-Ferrocenyl DNA End-Grafted on Gold", J. Am. Chem. Soc., 2006, 128, pp. 542-557.
Aradhya et al., "Single-molecule junctions beyond electronic transport", Nature Nanotechnology, vol. 8, Jun. 5, 2013, pp. 399-410.
Arbour, et al., "Surface Chemistries and Photoelectrochemistries of Thin Film Molecular Semiconductor Materials", Molecular Crystals and Liquid Crystals Incorporating Nonlinear Optics, vol. 183, 1990, Issue 1, pp. 307-320.
Arkin, et al., "Rates of DNA-Mediated Electron Transfer between Metallointercalators", Science, vol. 273, No. 5274, Jul. 26, 1996, pp. 475-480.
Arnold, et al., "DNA Charge Transport: from Chemical Principles to the Cell", Cell Chemical Biology Review, vol. 23, Jan. 21, 2016, pp. 183-197.
Artes, et al., "Conformational gating of DNA conductance", Nature communications, vol. 6, Dec. 9, 2015, article 8870, pp. 1-8.
Aviram, et al., "Molecular Rectifiers", Chemical Physics Letters, Nov. 15, 1974, vol. 29, No. 2, pp. 277-283.
Azhayev et al., "Amide group assisted 3'-dephosphorylation of oligonucleotides synthesized on universal A-supports", Tetrahedron, vol. 57, Issue 23, Jun. 4, 2001, pp. 4977-4986.

(56) References Cited

OTHER PUBLICATIONS

Bard, et al., "Electrochemical Methods: Fundamentals and Applications", 2nd ed., Wiley, New York, 2000, 850 pgs. (presented in three parts).
Batra et al., "Quantifying through-space charge transfer dynamics in π-coupled molecular systems", Nature Communications, vol. 3, Article 1086, Sep. 25, 2012, pp. 1-7.
Baumstark, et al., "Perylene Bisimide Dimers as Fluorescent "Glue" for DNA and for Base-Mismatch Detection", Angew. Chem. Int. Ed., 2008, vol. 47, DOI: 10.1002/anie.200705237, pp. 2612-2614.
Baumstark et al., "Fluorescent Hydrophobic Zippers inside Duplex DNA: Interstrand Stacking of Perylene-3,4:9,10-tetracarboxylic Acid Bisimides as Artificial DNA Base Dyes", Chemistry—A European Journal, vol. 14, Issue 22, Jul. 28, 2008, pp. 6640-6645.
Bjorneholm et al., "Determination of time scales for charge-transfer screening in physisorbed molecules", Physical Review Letters, vol. 68, Issue 12, Mar. 23, 1992, pp. 1892-1895.
Braun, et al., "Energy-Level Alignment at Organic/Metal and Organic/Organic Interfaces", Advanced Materials, 2009, vol. 21, pp. 1450-1472.
Brühwiler, et al., "Charge-transfer dynamics studied using resonant core spectroscopies", Rev. Mod. Phys., vol. 74, No. 3, Jul. 2002, pp. 703-740.
Burley et al., "Directed DNA Metallization", Journal of the American Chemical Society, vol. 128, No. 5, Jan. 12, 2006, pp. 1398-1399.
Cao, et al., "Charge transfer dynamics of 3,4,9,10-perylene-tetracarboxylic-dianhydride molecules on Au(111) probed by resonant photoemission spectroscopy", The Journal of Chemical Physics, vol. 135, Issue 17, Article 174701, Nov. 2011, pp. 174701-1-174701-7.
Cao et al., "Molecular Orientation and Site Dependent Charge Transfer Dynamics at PTCDA/TiO2(110) Interface Revealed by Resonant Photoemission Spectroscopy", The Journal of Physical Chemistry C, vol. 118, No. 8, Jan. 29, 2014, pp. 4160-4166.
Cao, et al., "Orbital dependent ultrafast charge transfer dynamics of ferrocenyl-functionalized SAMs on gold studied by core-hole clock spectroscopy", J. Phys. Condens. Matter, 2016, vol. 28, 094006, 10 pgs.
Cao et al., "Quantitative Femtosecond Charge Transfer Dynamics at Organic/Electrode Interfaces Studied by Core-Hole Clock Spectroscopy", Advanced Materials, vol. 26, Issue 46, Dec. 10, 2014, pp. 7880-7888.
Chen, et al., "Organic—Organic Heterojunction Interfaces: Effect of Molecular Orientation", Adv. Funct. Mater. 2011, vol. 21, pp. 410-424.
Chidsey, et al., "Coadsorption of Ferrocene-Terminated and Unsubstituted Alkanethiols on Gold: Electroactive Self-Assembled Monolayers", J. Am. Chem. Soc., 1990, vol. 112, No. 11, pp. 4301-4306.
Choi, "Hopping Transport in Long Conjugated Molecular Wires Connected to Metals", Charge and Exciton Transport through Molecular Wires (2011), pp. 61-91.
Choi, et al., "Transition from Tunneling to Hopping Transport in Long, Conjugated Oligo-imine Wires Connected to Metals", J. Am. Chem. Soc., 2010, vol. 132, No. 12, pp. 4358-4368.
Cohen, et al., "Direct measurement of electrical transport through single DNA molecules of complex sequence", PNAS, Aug. 16, 2005, vol. 102, No. 33, pp. 11589-11593.
Coropceanu, et al., "Charge Transport in Organic Semiconductors", Chem. Rev., 2007, vol. 107, pp. 926-952.
Coville, et al., "Molecular effects on inner-shell lifetimes: Possible test of the one-center model of Auger decay", Phys. Rev. A: At., Mol., Opt. Phys., Jun. 1, 1991, vol. 43, No. 11, pp. 6053-6056.
Davis et al., "Molecular-wire behaviour in p-phenylenevinylene oligomers", Nature, vol. 396, Nov. 5, 1998, pp. 60-63.
Davydova, et al., "Transient absorption microscopy: advances in chemical imaging of photoinduced dynamics", Laser Photonics, Rev. 10, No. 1, 2016), DOI 10.1002/lpor.201500181, pp. 62-81.
Dimitrov, et al., "Materials Design Considerations for Charge Generation in Organic Solar Cells", Chemistry of Materials, 2014, vol. 26, dx.doi.org/10.1021/cm402403z, pp. 616-630.
Dong, et al., "25th Anniversary Article: Key Points for High-Mobility Organic Field-Effect Transistors", Advanced Materials, 2013, vol. 25, pp. 6158-6183.
Dou, et al., "25th Anniversary Article: A Decade of Organic/Polymeric Photovoltaic Research", Advanced Materials, 2013, vol. 25, pp. 6642-6671.
Drummond, et al., "Electron Transfer Rates in DNA Films as a Function of Tether Length", J. Am. Chem. Soc., 2004, vol. 126, pp. 15010-15011.
Dunitz, et al., "How molecules stick together in organic crystals: weak intermolecular interactions", Chem. Soc. Rev., 2009, vol. 38, pp. 2622-2633.
Eckermann et al., "Electrochemistry of redox-active self-assembled monolayers", Coordination Chemistry Reviews, vol. 254, Issues 15-16, Aug. 1, 2010, pp. 1769-1802 (presented in two parts).
Eley, et al., "Semiconductivity of Organic Substances", Trans. Faraday Soc., 1962, vol. 58, pp. 411-415.
Enkovaara, "Electronic structure calculations with GPAW: a real-space implementation of the projector augmented-wave method", J. Phys. Condens. Matter, vol. 22, 2010, article 253202, pp. 1-24.
Ensslen et al., "One-Dimensional Multichromophor Arrays Based on DNA: From Self-Assembly to Light-Harvesting", Accounts of Chemical Research, Oct. 20, 2015, vol. 48, Issue 10, published online Sep. 28, 2015, pp. 2724-2733.
Fink, et al., "Electrical conduction through DNA molecules", Letters to Nature, vol. 398, Apr. 1, 1999, pp. 407-410.
Fischler et al., "Formation of Bimetallic Ag—Au Nanowires by Metallization of Artificial DNA Duplexes", Small, vol. 3, Issue 6, Jun. 4, 2007, pp. 1049-1055.
Floreano, et al., "Performance of the grating-crystal monochromator of the ALOISA beamline at the Elettra Synchrotron", Rev. Sci. Instrum., Oct. 1999, vol. 70, No. 10, pp. 3855-3864.
Floreano, et al., "Periodic Arrays of Cu-Phthalocyanine Chains on Au(110)", J. Phys. Chem. C, 2008, vol. 112, pp. 10794-10802.
Fratesi, et al., "High resolution NEXAFS of perylene and PTCDI: a surface science approach to molecular orbital analysis", Phys. Chem. Chem. Phys., 2014, vol. 16, pp. 14834-14844.
Frisch, et al., "Gaussian 09 (Revision D.01)", Electronic Supplementary Material (ESI) for Chemical Science, The Royal Society of Chemistry, Gaussian, Inc., Wallingford, CT, 2009, 20 pgs.
Gatty, et al., "Hopping versus Tunneling Mechanism for Long-Range Electron Transfer in Porphyrin Oligomer Bridged Donor-Acceptor Systems", J. Phys. Chem. B, Mar. 9, 2015, vol. 119, pp. 7598-7611.
Genereux, et al., "Mechanisms for DNA Charge Transport", Chem. Rev., Mar. 10, 2010, vol. 110, No. 3, 47 pgs.
Geng et al., "The interplay of intermolecular interactions, packing motifs and electron transport properties in perylene diimide related materials: a theoretical perspective", Journal of Materials Chemistry, vol. 22, Issue 39, Sep. 18, 2012, pp. 20840-20851.
Gerardi, "Electron injection at the PTCDA/metal interface detected by electron paramagnetic resonance", Chemical Physics Letters, vol. 593, 2014, pp. 45-47.
Giacalone, et al., "Exceptionally Small Attenuation Factors in Molecular Wires", J. Am. Chem. Soc., 2004, vol. 126, No. 17, pp. 5340-5341.
Gilbert, et al., "Photoinduced charge and energy transfer in molecular wires", Chem. Soc. Rev., 2015, vol. 44, pp. 845-862.
Gorl, et al., "Molecular Assemblies of Perylene Bisimide Dyes in Water", Angew. Chem. Int. Ed., 2012, vol. 51, pp. 6328-6348.
Gorodetsky, et al., "DNA-Mediated Electrochemistry", Bioconjugate Chem., Dec. 2008, vol. 19, No. 12, pp. 2285-2296.
Gsänger, et al., "Organic Semiconductors based on Dyes and Color Pigments", Adv. Mater., 2016, vol. 28, pp. 3615-3645.
Guldi et al., "Molecular wires", Chemical Society Reviews, vol. 44, Issue 4, Feb. 21, 2015, first published Jan. 30, 2015, pp. 842-844.
Hariharan et al., "Hydrophobic Dimerization and Thermal Dissociation of Perylenediimide-Linked DNA Hairpins", Journal of the American Chemical Society, vol. 131, Issue 16, Apr. 1, 2009, pp. 5920-5929.

(56) References Cited

OTHER PUBLICATIONS

Harris, et al., "Further Conventions for NMR Shielding and Chemical Shifts", Pure Appl. Chem., 2008, vol. 80, No. 1, pp. 59-84.
Hill, et al., "Molecular level alignment at organic semiconductor-metal interfaces", Appl. Phys. Lett., vol. 73, No. 5, Aug. 3, 1998, pp. 662-664.
Hirose, et al., "Chemistry and electronic properties of metal-organic semiconductor interfaces: Al, Ti, In, Sn, Ag, and Au on PTCDA", Physical Review B, vol. 54, No. 19, Nov. 15, 1996, pp. 13748-13758.
Huang et al., "Perylene-3,4,9,10-tetracarboxylic Acid Diimides: Synthesis, Physical Properties, and Use in Organic Electronics", The Journal of Organic Chemistry, vol. 76, Issue 8, 2011, web publication date Mar. 16, 2011, pp. 2386-2407.
Hüsken, et al., "Mechanistic Studies of Fc-PNA (DNA) Surface Dynamics Based on the Kinetics of Electron-Transfer Processes", Chem. Eur. J., 2011, vol. 17, pp. 9678-9690.
Hwang, et al., "Energetics of metal-organic interfaces: New experiments and assessment of the field", Materials Science and Engineering R, vol. 64, 2009, pp. 1-31.
Ishii, et al., "Energy Level Alignment and Interfacial Electronic Structures at Organic/Metal and Organic/Organic Interfaces", Adv. Mater., 1999, vol. 11, No. 8, pp. 605-625.
Jang, et al., "Effects of the permanent dipoles of self-assembled monolayer-treated insulator surfaces on the field-effect mobility of a pentacene thin-film transistor", Appl. Phys. Lett., vol. 90, 2007, 4 pgs.
Jia et al., "Carbon Electrode-Molecule Junctions: A Reliable Platform for Molecular Electronics", Accounts of Chemical Research, vol. 48, Issue 9, Jul. 20, 2015, pp. 2565-2575.
Jong, et al., "Femtosecond Charge Transfer in Assemblies of Discotic Liquid Crystals", J. Phys. Chem. C, 2008, vol. 112, pp. 15784-15790.
Jung et al., "Molecular Design and Synthetic Approaches to Electron-Transporting Organic Transistor Semiconductors", Chemistry of Materials, vol. 23, Issue 3, 2011, web publication date Oct. 22, 2010, pp. 568-582.
Kahn, Antoine "Fermi level, work function and vacuum level", Mater. Horiz., 2016, vol. 3, pp. 7-10.
Kao, et al., "Charge Transfer Time in Alkanethiolate Self-Assembled Monolayers via Resonant Auger Electron Spectroscopy", J. Phys. Chem. C, vol. 114, No. 32, 2010, pp. 13766-13773.
Karis et al., "One-Step and Two-Step Description of Deexcitation Processes in Weakly Interacting Systems", Physical Review Letters, vol. 76, Issue 8, Feb. 19, 1996, pp. 1380-1383.
Kasumov et al., "Proximity-Induced Superconductivity in DNA", Science, vol. 291, 280, Jan. 12, 2001, DOI: 10.1126/science.291.5502.280, 4 pgs.
Kato, et al., "Electronic Structure of Bases in DNA Duplexes Characterized by Resonant Photoemission Spectroscopy Near the Fermi Level", Physical Review Letters, Aug. 20, 2004, vol. 93, No. 8, 4 pgs.
Kazmaier et al., "A Theoretical Study of Crystallochromy. Quantum Interference Effects in the Spectra of Perylene Pigments", Journal of the American Chemical Society, vol. 116, No. 21, Oct. 1994, pp. 9684-9691.
Kelley, et al., "Weitreichender Elektronentransfer durch DNA-Filme", Angew. Chem., 1999, vol. 111, Nr. 7, pp. 991-996.
Keren et al., "Patterned DNA Metallization by Sequence-Specific Localization of a Reducing Agent", Nano Letters, vol. 4, No. 2, Jan. 3, 2004, pp. 323-326.
Kim, et al., "One-Dimensional Nanostructures of π-Conjugated Molecular Systems: Assembly, Properties, and Applications from Photovoltaics, Sensors, and Nanophotonics to Nanoelectronics", Chemistry of Materials Review, 2011, 23, DOI:10. 1021/cm102772x, pp. 682-732.
Kozma, et al., "Perylene diimides based materials for organic solar cells", Dyes Pigm., 2013, vol. 98, pp. 160-179.

Laviron, "General Expression of the Linear Potential Sweep Voltammogram in the Case of Diffusionless Electrochemical Systems", J. Electroanal. Chem., 1979, vol. 101, pp. 19-28.
Lee, et al., "Effect of the Phase States of Self-Assembled Monolayers on Pentacene Growth and Thin-Film Transistor Characteristics", J. Am. Chem. Soc., 2008, vol. 130, pp. 10556-10564.
Lee, et al., "Ferrocenylalkylthiolates as a Probe of Heterogeneity in Binary Self-Assembled Monolayers on Gold", Langmuir, 2006, vol. 22, pp. 4438-4444.
Lee, et al., "Interfacial electronic structure for high performance organic devices", Current Applied Physics, vol. 16, 2016, pp. 1533-1549.
Lee, et al., "Surface Coverage and Structure of Mixed DNA/Alkylthiol Monolayers on Gold: Characterization by XPS, NEXAFS, and Fluorescence Intensity Measurements", Anal. Chem., 2006, vol. 78, pp. 3316-3325.
Levicky, et al., "Using Self-Assembly to Control the Structure of DNA Monolayers on Gold: A Neutron Reflectivity Study", J. Am. Chem. Soc., 1998, vol. 120, pp. 9787-9792.
Li, et al., "Perylene Imides for Organic Photovoltaics: Yesterday, Today, and Tomorrow", Adv. Mater., 2012, vol. 24, pp. 613-636.
Li, et al., "Quasi-Ohmic Single Molecule Charge Transport through Highly Conjugated meso-to-meso Ethyne-Bridged Porphyrin Wires", Nano Lett., 2012, vol. 12, No. 6, pp. 2722-2727.
Lima, et al., "Electronic Structure of Self-Assembled Monolayers Modified with Ferrocene on a Gold Surface: Evidence of Electron Tunneling", J. Phys. Chem. C, 2014, vol. 118, No. 40, pp. 23111-23116.
Liu, et al., "Contact engineering in organic field-effect transistors", Materials Today, vol. 18, No. 2, Mar. 2015, pp. 79-96.
Lloveras, et al., "Tunneling versus Hopping in Mixed-Valence Oligo-p-phenylenevinylene Polychlorinated Bis(triphenylmethyl) Radical Anions", J. Am. Chem. Soc., 2011, vol. 133, pp. 5818-5833.
Loli, et al., "Growth of N,N'-Bis(1-ethylpropyl)perylene-3,4,9,10-tetracarboxdiimide Films on Ag (111)", J. Phys. Chem. C, 2009, vol. 113, pp. 17866-17875.
Love, et al., "Self-Assembled Monolayers of Thiolates on Metals as a Form of Nanotechnology", Chem. Rev., 2005, vol. 105, pp. 1103-1169.
Luo, et al., "Recent Advances in Organic Photovoltaics: Device Structure and Optical Engineering Optimization on the Nanoscale", Small, vol. 12, Issue 12, Mar. 23, 2016, pp. 1547-1571.
Markegard et al., "Molecular Dynamics Simulations of Perylenediimide DNA Base Surrogates", The Journal of Physical Chemistry B, vol. 119, Issue 35, Aug. 21, 2015, pp. 11459-11465.
Mazaheripour, et al. "Unexpected length dependence of excited-state charge transfer dynamics for surface-confined perylenediimide ensembles" Mater. Horiz., 2017, vol. 4, pp. 437-441.
McCreery, et al., "A critical perspective on molecular electronic junctions: there is plenty of room in the middle", Phys. Chem. Chem. Phys., 2013, vol. 15, pp. 1065-1081.
Menzel, et al., "Ultrafast charge transfer at surfaces accessed by core electron spectroscopies", Chem. Soc. Rev., 2008, vol. 37, pp. 2212-2223.
Momma, et al., "VESTA 3 for three-dimensional visualization of crystal, volumetric and morphology data", Journal of Applied Crystallography, 2011, vol. 44, doi:10.1107/S0021889811038970, pp. 1272-1276.
Mortensen, et al., "Real-space grid implementation of the projector augmented wave method", Physical Review B, vol. 71, 2005, pp. 035109-1-035109-11.
Mucic, et al., "Synthesis and characterization of DNA with ferrocenyl groups attached to their 5'-termini: electrochemical characterization of a redox-active nucleotide monolayer", Chem. Commun., 1996, pp. 555-557.
Murawski, et al., "Efficiency Roll-Off in Organic Light-Emitting Diodes", Advanced Materials, 2013, vol. 25, pp. 6801-6827.
Muren, et al., "Solution, surface, and single molecule platforms for the study of DNA-mediated charge transport", Phys. Chem. Chem. Phys., Oct. 28, 2012, vol. 14, No. 40, doi:10.1039/c2cp41602f, pp. 13754-13771.

(56) References Cited

OTHER PUBLICATIONS

Newton et al., "Interfacial bridge-mediated electron transfer: mechanistic analysis based on electrochemical kinetics and theoretical modelling", Physical Chemistry Chemical Physics, vol. 9, Issue 5, 2007, published online Oct. 30, 2006, pp. 555-572.
Nichols et al., "Single-Molecule Electronics: Chemical and Analytical Perspectives", Annual Review of Analytical Chemistry, vol. 8, Jul. 2015, published online Jun. 1, 2015, pp. 389-417.
Odenthal, et al., "An introduction to electrochemical DNA biosensors", Analyst, 2007, vol. 132, pp. 603-610.
Ofir et al., "Nanoimprint Lithography for Functional Three-Dimensional Patterns", Advanced Materials, vol. 22, Issue 32, Aug. 24, 2010, pp. 3608-3614.
Ohkita, et al., "Exciton and Charge Dynamics in Polymer Solar Cells Studied by Transient Absorption Spectroscopy", Organic Solar Cells, Green Energy and Technology, ed. W. C. H. Choy, Springer-Verlag, London, England, 2013, pp. 103-137.
Ohkita, et al., "Transient absorption spectroscopy of polymer-based thin-film solar cells", Polymer, vol. 52, 2011, pp. 4397-4417.
Ohno, "Deexcitation processes in adsorbates", Phys. Rev. B, Jul. 15, 1994, vol. 50, issue 4, pp. 2566-2575.
Ostroverkhova, "Organic Optoelectronic Materials: Mechanisms and Applications", Chem. Rev., 2016, vol. 116, pp. 13279-13412.
Palma et al., "Controlled confinement of DNA at the nanoscale: nanofabrication and surface bio-functionalization", DNA Nanotechnology: Methods and Protocols, Methods in Molecular Biology, vol. 749, May 19, 2011, pp. 169-185.
Palma et al., "Selective Biomolecular Nanoarrays for Parallel Single-Molecule Investigations", Journal of the American Chemical Society, vol. 133, Issue 20, Apr. 29, 2011, pp. 7656-7659.
Reese, "Oligo- and poly-nucleotides: 50 years of chemical synthesis", Org. Biomol. Chem., 2005, vol. 3, pp. 3851-3868.

R = O, N

R$^{1-2}$ = H, alkyl, aryl, Newkome-type carboxylates, phosphate surfactants, polyglycerol dendrons, cyclodextrin, R$^{3-6}$ = H, F, Cl, Br, CN, alkyl, aryl, aryloxy, T¹ = Terminus 1
T² = Terminus 2

T¹ = Terminus 1
T² = Terminus 2

Stacking for Black-Colored Crystals

Stacking for Red-Colored Crystals

CONTROLLED SYNTHESIS OF POLYMERIC PERYLENE DIIMIDE AND APPLICATIONS THEREOF

CROSS REFERENCE TO RELATED APPLICATIONS

This application claims priority to U.S. Provisional Application Ser. No. 62/396,020, filed Sep. 16, 2016, which is incorporated herein by reference in its entirety.

FIELD OF THE INVENTION

The current disclosure is directed to compounds and methods for controlled synthesis of polymeric perylene diimide derivatives and applications thereof.

BACKGROUND OF THE INVENTION

Perylene-containing compounds, such as perylene diimide (PDI) derivatives, are dyes possessing intense visible light absorption, high photochemical and air stability, strong electron-accepting ability, and near-unity fluorescence quantum yields. These advantageous properties are derived from PDIs' molecular structure, based on a rigid, fused aromatic core, which favors π-π intermolecular interactions, and is highly amenable to functionalization (See FIG. 1). Collectively, their outstanding chemical and physical properties make perylene derivatives attractive as pigments, materials for optoelectronic devices, and fluorescent labels for biological systems.

Due to their optical characteristics, as well as excellent chemical, photo, thermal, and mechanical stabilities, perylene diimides have long established themselves as important industrial pigments, especially in textile and high-grade paint industries. However, more recently, new applications for PDI derivatives have emerged in conjunction with their favorable photophysical and electronic properties, such as high molar absorption coefficients, reversible redox chemistry, and excellent charge transport behavior. For example, certain PDI derivatives have attracted interest as photovoltaic functional materials, as they exhibit n-type behavior, strong electron-accepting character, and high electron mobilities. To date, PDIs in general have been utilized in various types of optical and electronic devices, as diverse as organic field-effect transistors (OFETs), fluorescent solar collectors, electrophotographic systems, dye-based lasers, and organic photovoltaic cells (OPVs).

BRIEF SUMMARY OF THE INVENTION

Many embodiments of the invention are directed to an engineered perylene diimide polymer having a phosphate backbone that comprises:

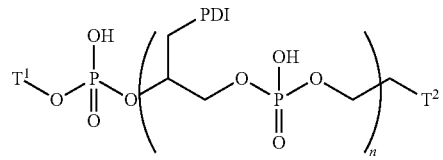

such that T1 and T2 are termini; n is a positive integer; and PDI is a perylene diimide that comprises:

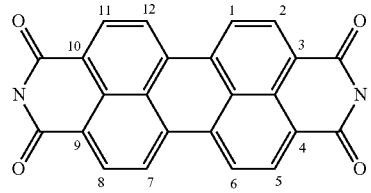

such that N is an imide, and a first imide is covalently linked to the phosphate backbone; a second imide is functionalized with a substituent selected from the group consisting of H, alkyl, aryl, polyethylene glycol, Newkome-type carboxylates, phosphate surfactants, polyglycerol dendrons, and clycodextrin; and positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups.

In further embodiments, the polymer is engineered to a precise length and sequence such that a collection of polymers is monodisperse.

In more embodiments, n is equal to four.

In even further embodiments, n is greater than 20.

In even more embodiments, n is greater than 100.

In even further more embodiments, at least two perylene diimides, each having a different chemical structure, are incorporated into the polymer.

In even further more embodiments, the polymer has an engineered sequence of perylene diimides.

In even further more embodiments, at least one perylene diimide is functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least one perylene diimide is functionalized on a second imide with polyethylene glycol.

In even further more embodiments, at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least two perylene diimides are functionalized on a second imide with polyethylene glycol.

In even further more embodiments, T1 and T2 are each independently selected from the group consisting of an amino group, a hydroxyl group, a carbonyl group, ferrocene and thiol.

Many embodiments of the invention are directed to a method of forming a perylene diimide polymer having a phosphate backbone that comprises providing a plurality of perylene diimides that comprises:

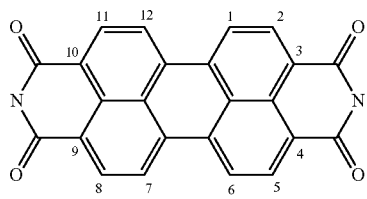

such that N is an imide, and such that a first imide is covalently linked to a phosphate functionality, a second imide is functionalized with a substituent selected from the group consisting of H, alkyl, aryl, polyethylene glycol, Newkome-type carboxylates, phosphate surfactants, polyglycerol dendrons, and clycodextrin; and positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups.

The method further comprises iteratively and sequentially linking a plurality of the perylene diimides through via the phosphate functionality to form the phosphate backbone through a nucleoside polymerization protocol such that a specific arrangement and number, n, of perylene diimides is obtained, and selectively terminating the polymer with termini T1 and T2.

In further embodiments, n is equal to four.

In more embodiments, n is greater than 20.

In even further embodiments, n is greater than 100.

In even more embodiments, the phosphate is a phosphoramidite.

In even further more embodiments, at least two perylene diimides, each having a different chemical structure, are incorporated into the polymer.

In even further more embodiments, at least one perylene diimide is functionalized on a position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least one perylene diimide is functionalized on a second imide with polyethylene glycol.

In even further more embodiments, at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least two perylene diimides are functionalized on a second imide with polyethylene glycol.

In even further more embodiments, T1 and T2 are each independently selected from the group consisting of an amino group, a hydroxyl group, a carbonyl group, ferrocene and thiol.

Many embodiments of the invention are directed to an organic nanowire that comprises a perylene diimide polymer having a phosphate backbone that comprises:

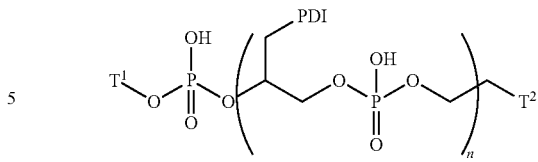

such that T1 and T2 are termini; n is a positive integer; and PDI is a perylene diimide comprising:

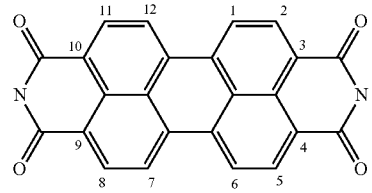

such that N is an imide, and a first imide is covalently linked to the phosphate backbone; a second imide is functionalized with a substituent selected from the group consisting of H, alkyl, aryl, polyethylene glycol, Newkome-type carboxylates, phosphate surfactants, polyglycerol dendrons, and clycodextrin; and positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups.

In further embodiments, the polymer is engineered to a precise length and sequence such that a collection of polymers is monodisperse.

In more embodiments, at least two perylene diimides, each having a different chemical structure, are incorporated into the polymer.

In even further embodiments, at least one perylene diimide is functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even more embodiments, at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

In even further more embodiments, T1 and T2 are each independently selected from the group consisting of an amino group, a hydroxyl group, a carbonyl group, ferrocene and thiol.

In even further more embodiments, the organic nanowire is incorporated into an electronic device.

In even further more embodiments, the electronic device is an organic field-effect transistor.

BRIEF DESCRIPTION OF THE DRAWINGS

The description will be more fully understood with reference to the following figures, which are presented as exemplary embodiments of the invention and should not be construed as a complete recitation of the scope of the invention, wherein.

DETAILED DESCRIPTION OF THE INVENTION

Turning now to the drawings, perylene diimide derivatives (PDI) and methods for controlled synthesis of polymeric PDI and applications thereof are provided. Many embodiments are directed to compounds that comprise at least an electronically active base surrogate and a solubility chain. In various embodiments the base surrogate is comprised of an electrochemically active perylene diimide molecule. In various embodiments the solubility chain comprises a PEG functionality, such as, for example, as an imide or other substituent to provide water and organic solvent solubility. In various embodiments, the PDI further comprises a phosphate functionality as an imide (e.g., phosphoramidite) or other substituent. In some such embodiments the phosphate functionality may be used as a chemical coupling building block to polymerize PDI molecules. In some of these embodiments, an oligonucleotide synthesizer is used for controlled polymerization. In many embodiments one or more aromatic core functionalizations may be incorporated into the PDI molecules to allow for tuning the molecule's electronic properties. In various embodiments one or more functional terminal groups may be incorporated into the PDI molecules, such as, for example terminal thiols for attachment to gold substrates and terminal ferrocenes for electrochemical measurements, among others.

Embodiments are also directed to methods of using the PDI molecules as a building-block to produce length and sequence controlled π-stacked PDI polymers that may be used as organic molecular wires. In many such embodiments the PDI phosphoramidite molecules may be incorporated into existing automated phosphoramidite polymer synthesizers in both water and organic solvents to yield PDI polymers having a phosphate backbone. Further embodiments are directed to precise control of length, sequence, and terminal functionality using an automated synthesizer such that self-assembly of the wires into variable configurations may be provided. In various embodiments molecular wires formed using such PDI molecules show no resistance loss with increasing length, allowing for their use in a variety of miniaturized electronics. In many such embodiments the molecular wires may be formed to be soluble in a variety of solvents, including organic solvents and water such that they may be processed and purified using many conventional techniques, including, for example, standard DNA/biochemistry techniques (e.g., reverse-phase HPLC).

Finally, embodiments are also directed to various synthetic methods for producing the PDI molecules and PDI polymers formed from such PDI molecules.

PDI Derivative Compounds and Polymers

Figure 1:
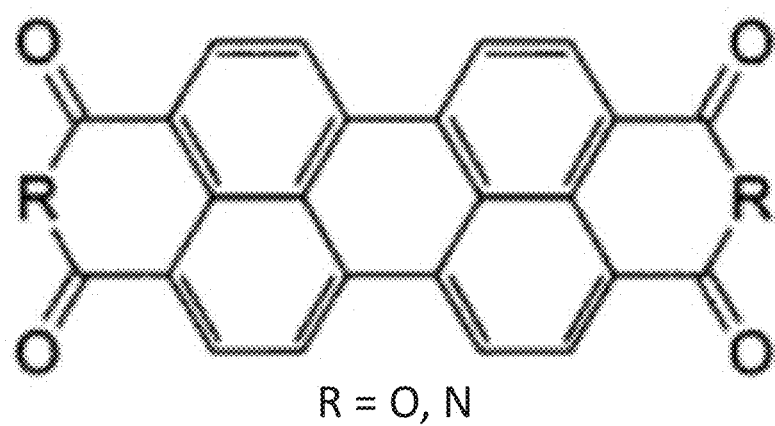
FIG. 1 provides a molecular structure diagram of two PDI molecules, Perylene-3,4,9,10-tetracarboxylic acid diimide (PTCDI) and Perylene-3,4,9,10-tetracarboxylic dianhydryde (PTCDA), used as dye molecules in the prior art.
Figure 2:
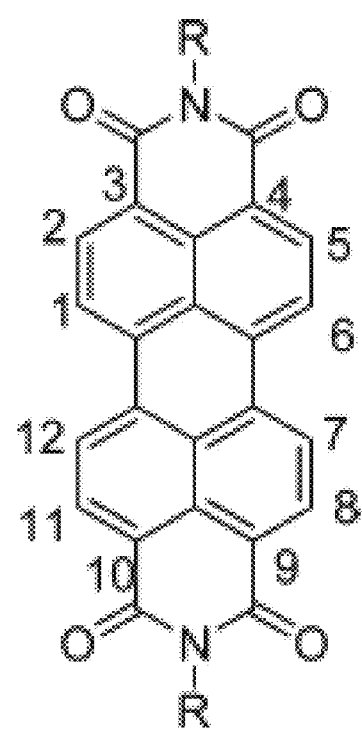
FIG. 2 provides a molecular structure diagram of a PDI molecule having functionalization at the imide positions, in accordance of various embodiments of the invention.

Perylene-3,4,9,10-tetracarboxylic acid diimide derivatives (abbreviated PTCDIs; also commonly called perylene diimides and abbreviated as PDIs), shown in FIG. 2, have been extensively studied as industrial colorants, both as dyes (soluble) and pigments (insoluble). This family of molecules possesses well-known electrochemical properties, a propensity for adapting 7-conjugated stacked columnar arrangements, and excellent stability under adverse conditions. (See, e.g., F. Würthner, Chem. Commun. 2004, 1564-1579.; and C. Huang, S. Barlow, S. R. Marder, J. Org. Chem. 2011, 76, 2386-2407; the disclosures of which are incorporated herein by reference.) Moreover, various embodiments PDIs with different chemical and physical properties can be obtained by modification of the substituents. In some of these embodiments, substituents can be inserted in the imide N, N' positions and/or the 1, 6, 7, and/or 12 positions of the hydrocarbon core (the so called "bay" positions) (FIG. 2). In particular, embodiments are direct to influencing PDI's solubility and propensity for aggregation via functionalization at imide positions (including with two different substituents) and other embodiments involve tuning HOMO-LUMO levels via substitutions at the bay positions. These advantageous chemical and physical properties as well as high molecular modularity make PDI derivatives attractive synthetic targets for electron charge transport materials.

As shown in FIG. 2, the PDI derivatives in accordance with embodiments at least incorporate substituents along the base perylene and/or at one or both of the imide functionalities. Some of these embodiments are directed to the incorporation of a solubility tail that keeps the PDIs from aggregating or precipitating out of organic solvents and/or water. In some embodiments, PDI molecules are functionalized with alkyl or aryl substituents on the imides. In accordance with several other embodiments, a PDI derivative is functionalized on an imide with hydrophilic moieties, which may include a polyethylene glycol (PEG) solubility tail, Newkome-type carboxylates, phosphate surfactants, polyglycerol dendrons, and clycodextrin. In many such embodiments, one imide is functionalized with one moiety and the other imide is functionalized with another, resulting in an unsymmetrical PDI molecule (See FIG. 3). In many such embodiments, an unsymmetrical PDI molecule has a phosphate group (e.g., phosphoramidite) covalently linked to a first imide and a second functionality (e.g., PEG polymer) on a second imide. PEG functionalization, however, in accordance with several embodiments, may be performed anywhere along the perylene molecules including one of the imide moieties, or bay positions (See FIG. 3). Furthermore, in accordance with a number of embodiments, the number and/or length of PEG functionalities attached to a PDI molecule can vary, depending on the need and or function. For example, longer PEG chains may be preferred on either imide moiety as a longer PEG functionality extending from the bay position may interfere with base stacking between PDI molecules. In several embodiments, a PEG moiety may be attached to the PDI in one synthetic step.

PEG is an inexpensive polymer widely adapted in applications ranging from industrial manufacturing to medicine. One distinctive property of these organic neutral compounds is their good solubility in both water and many common organic solvents, such as methanol, ethanol, acetonitrile, benzene, and dichloromethane. PEG also allows for the tuning of the solubility of the molecules as longer (more repeat units of ethylene glycol) PEG chains may impart stronger hydrophilicity. Functionalization with PEG, in accordance with embodiments can significantly expand the scope of PDIs' applications.

Figure 3:
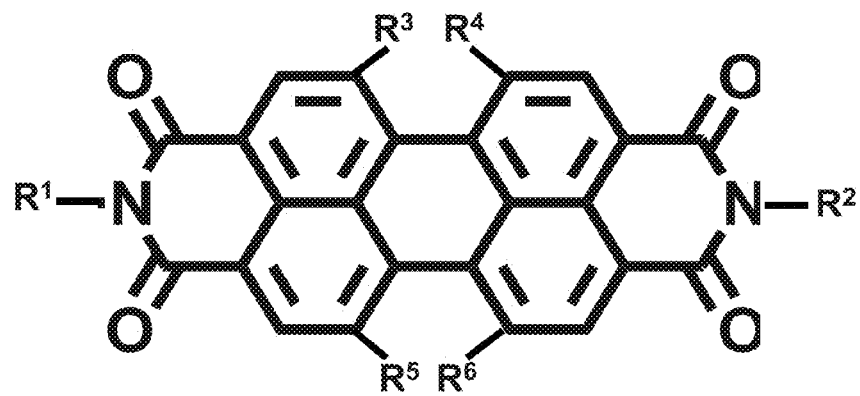
FIG. 3 provides a molecular structure diagram depicting a PDI molecule and potential for modification of the molecule's physical properties via functionalization, in accordance with various embodiments of the invention.
Figure 3:
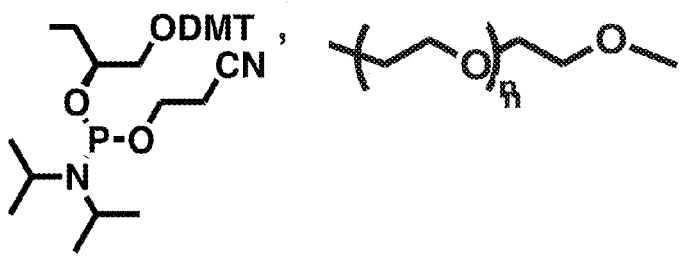
Figure 3:
Figure 3:
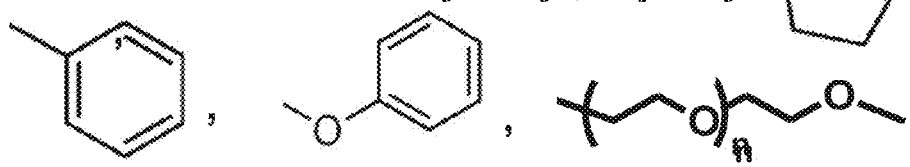

In many embodiments, the core perylene of the PDI derivatives may be further substituted along its body (e.g., at the "bay" positions disposed at positions 1 & 12 and 6 & 7; See FIG. 2) to further increase solubility and/or to allow for the configuration of highly modular PDI derivative compounds with easily tunable physical and chemical properties (See FIG. 3) (See C. Huang, S. Barlow, and S. R. Marder, 2011, cited supra). In particular, as shown in the figure, PDI derivatives with symmetrical or unsymmetrical imide substituents may be produced that allow for the further chemical modification of the perylene core. As shown in FIG. 3, the bay positions can be modified with halogens (e.g., F, Cl, Br), cyanides, alkyl groups, aryl groups, aryloxy groups, and PEG polymers. For example, the introduction of aryl, aryloxy, or bromo groups can influence steric interactions between the PDI molecules, disrupting $\pi$-$\pi$ stacking, which can improve solubility. It should be understood that any substituents that may disrupt the $\pi$-$\pi$ stacking, such as bulky groups, would be expected to increase solubility. On the other hand, severe disruption of $\pi$-$\pi$ stacking may interfere with the electron transfer properties of the molecules, and thus proper balance between solubility and electrochemical properties needs to be considered.

Figure 4:
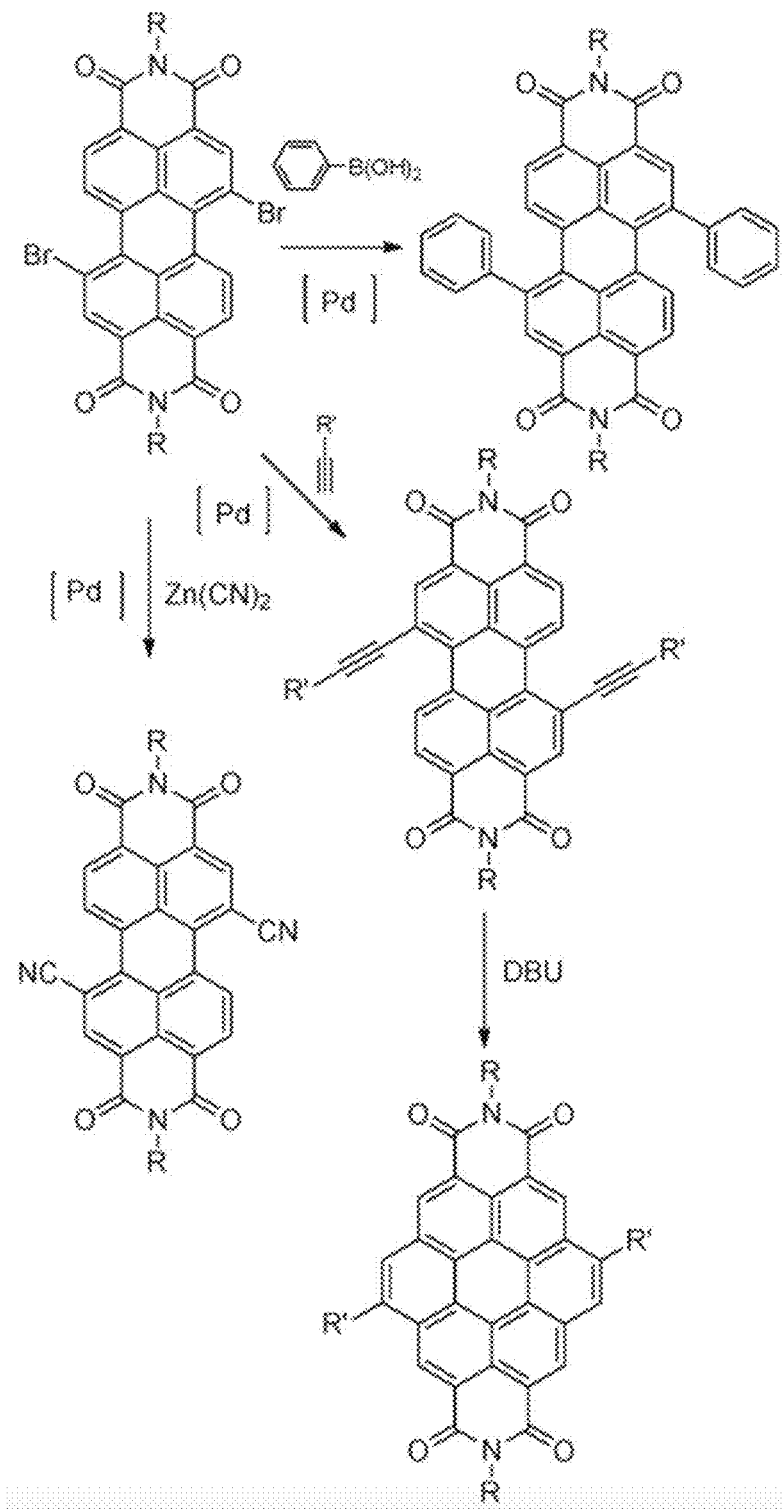
FIG. 4 provides a molecular structure diagrams depicting the modular nature of a perylene diimide core and potential for modification of the molecule's physical properties via core functionalization, in accordance with the embodiments of the invention.

In various embodiments, dibrominated and tetrachlorinated soluble PDIs may be used as intermediates for the synthesis of a wide variety of di- and tetra-substituted derivatives (e.g., cyano, fluoride, phenoxy, and amino groups) via nucleophilic substitution reactions, as is described in greater detail in the Exemplary Embodiments (See also FIG. 4). Nucleophilic substitutions of bromo bay substituents can be performed via of known protocols and often have high yields. Fluoride-, cyanide-, phenol, and amine-based nucleophiles can be incorporated to create variety of PDI molecules having unique electronic properties due to the significant electronic coupling between the substituents and PDI cores.

A variety of diaryl- and tetraaryl-functionalized PDIs may also be formed via transition-metal catalyzed C—C couplings, such as Suzuki, Stille, and Sonogashira reactions, yielding aryl, heteroaryl, and akynyl functionalized PDIs couplings at the aryl halide positions (FIG. 4). Such processes allow for facile substitution of the perylene core with a wide range of electron-withdrawing groups and electron-donating groups, allowing for modulation of the electronic properties of our PDI building blocks. (For further detailed information see, e.g., Wagenknecht, H-A. *Curr. Org. Chem.* 2004, 8, 251-266; Würthner, F. *Chem. Commun.* 2004, 1564-1579; Jung, B. J.; et al. *Chem. Mater.* 2011, 23, 568-582; and Huang, C.; Barlow, S.; Marder, S. R. *J. Org. Chem.*, 2011, 76, 2386-2407, the disclosures of which are incorporated herein by reference.)

Although modifications of bay positions (i.e., position 1, 6, 7, and 12) are described in detail, it should be noted that the other positions of the perylene core (e.g., 2, 5, 8, 11) can also be substituted. For example, direct arylation or alkylation of positions 2, 5, 8, and 11 have been reported (See, C. Huang, S. Barlow, and S. R. Marder, 2011, cited supra). Substitutions at these positions may yield desired solubility without great distortion of $\pi$-$\pi$ stacking and thus may benefit electronic coupling between molecules.

Figure 5:
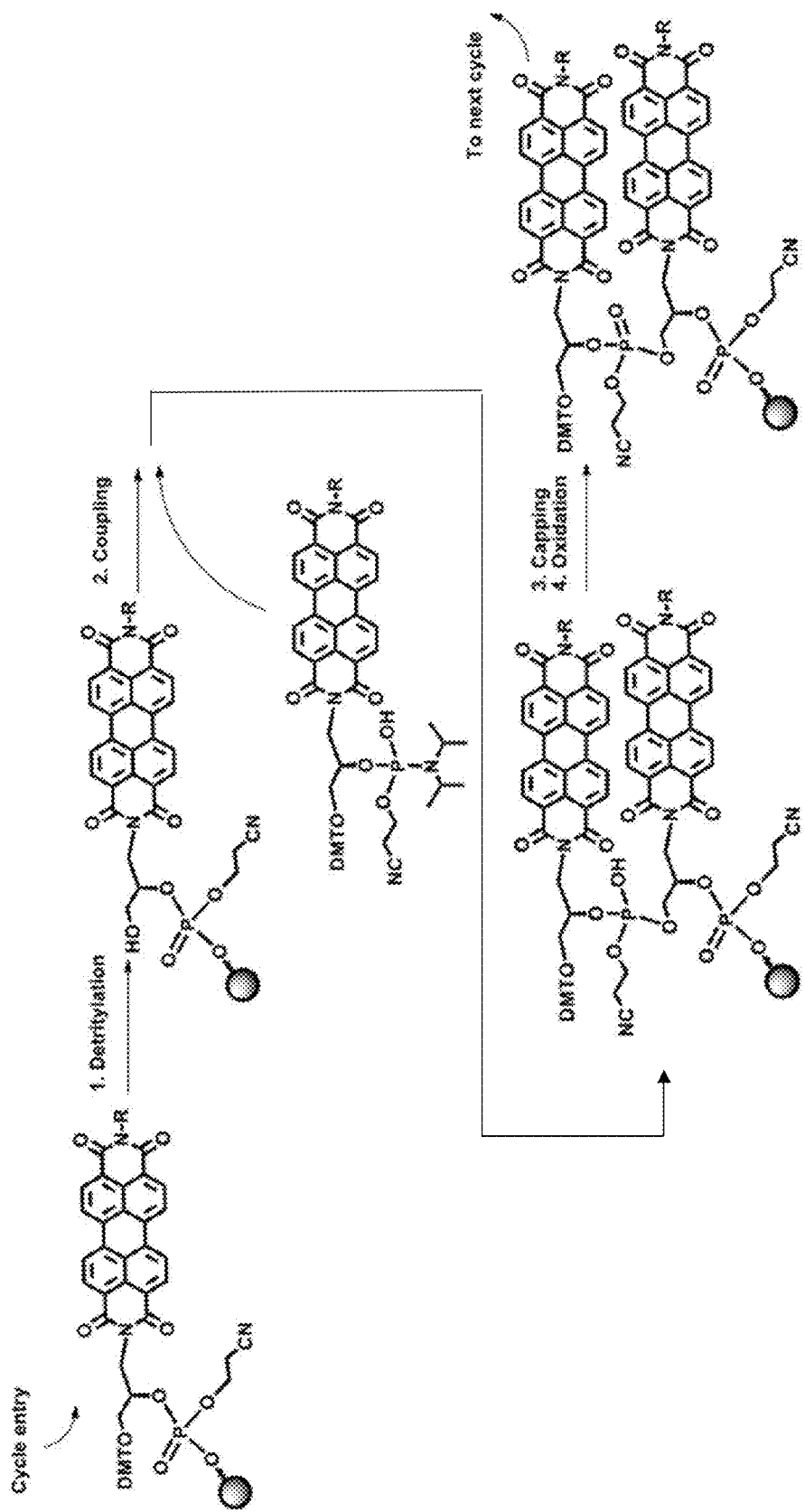
FIG. 5 provides a schematic diagram depicting polymerization of phosphoramidite PDI via phosphate linkers, in accordance with various embodiments of the invention.
Figure 6A:
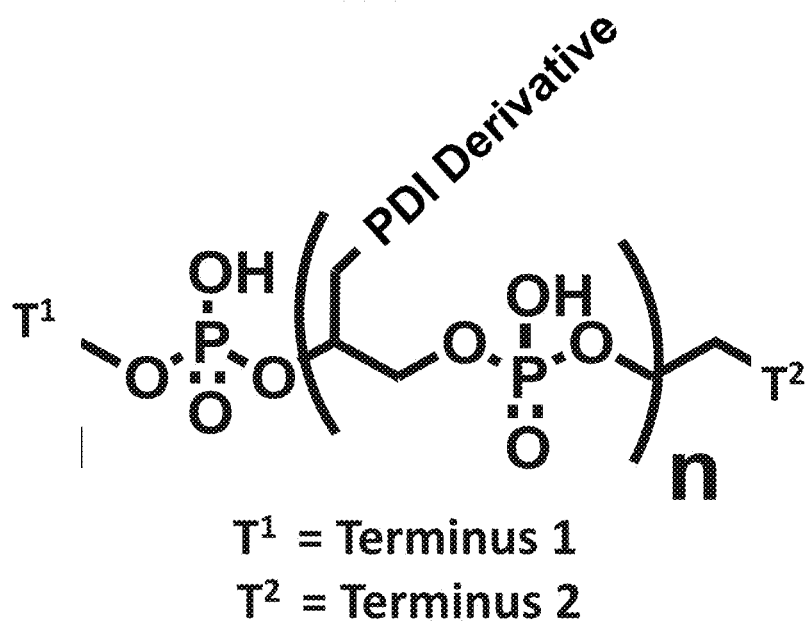
FIG. 6A provides a molecular structure diagram of PDI polymers linked via phosphates and having functionalized termini, in accordance with various embodiments of the invention.
Figure 6B:
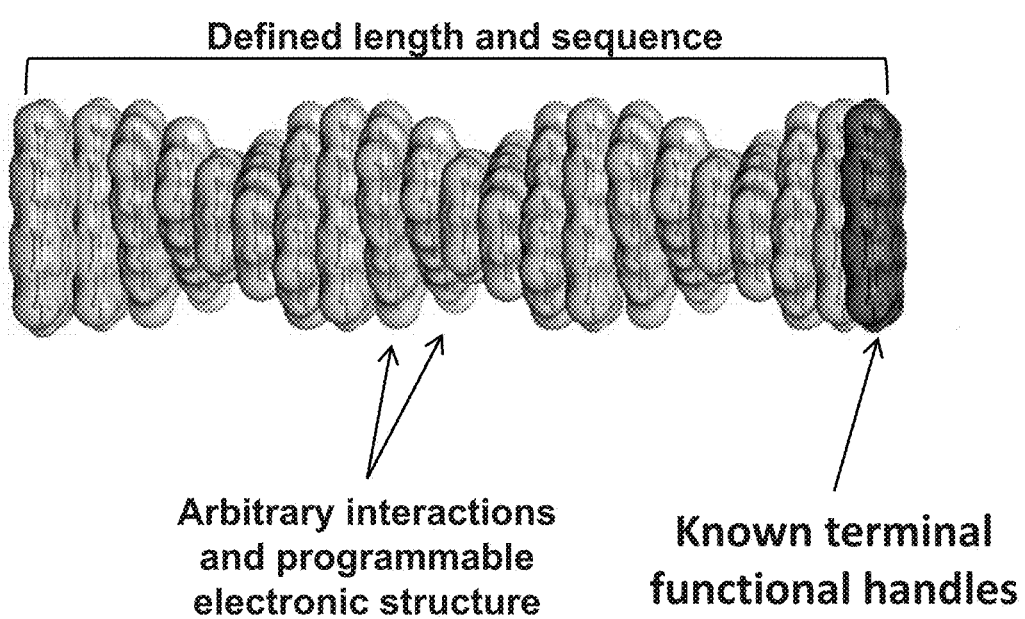
FIG. 6B provides a schematic diagram of PDI polymers having defined length and sequence with functionalized termini, in accordance with various embodiments of the invention.

Numerous embodiments are also directed to soluble, multifunctional PDI derivatives for use in a wide-variety of applications, including as building-blocks for polymers that can be used as molecular wires. In such embodiments the PDI serves as a central electroactive component. To build polymeric PDI molecules, various embodiments of PDI molecules may include a phosphate functionality (e.g., phosphoramidite) extended from at least one imide of the perylene core (See FIG. 3). Accordingly, incorporation of a phosphoramidite (or similar) group allows for PDI compounds be used as nucleoside-phosphoramidite-like base-surrogates to be polymerized along a phosphate backbone by various nucleoside polymerization protocols, which may include the use of an oligosynthesizer. FIG. 5 displays a typical polymerization scheme with the use of phosphoramidite PDI derivatives. It should be noted that for the sake of simplicity, FIG. 5 depicts polymerization of phosphoramidite PDI derivatives having the perylene core without any additional functionalization, but the PDI derivative can be modified as described in previous paragraphs, including functionalization of an amide and/or bay positions. Accordingly, polymerization results in various embodiments of PDI polymers having various PDI derivative units (FIGS. 6A and 6B). In several embodiments, a PDI derivative unit has a phosphoramidite covalently linked to a first imide, such that the phosphoramidite functions to iteratively link the PDI derivative to a PDI polymer. Some of such embodiments will also have a functionality (e.g., PEG polymer) extending from a second imide. In many more embodiments, PDI polymers, regardless of polymerization method, are capable of base stacking via the aromatic $\pi$ bonds, creating stable long polymers with high electron transfer capabilities.

Automated nucleic acid synthesizing protocols and equipment are designed to chemically couple nucleoside phosphoramidites to synthesize a sequence of nucleic acid polymers in vitro. Nucleoside phosphoramidites, which may feature a natural or designer oligonucleotide base, can be used to build natural and artificial oligonucleotides. Accordingly, oligonucleotide polymerization can iteratively combine provided phosphoramidites in any user-designed order, allowing for construction of known natural oligonucleotide sequences or user-defined artificial variants—all with exquisite precision and in a relatively fast, inexpensive manner. It has now been determined that functionalized PDI phosphoramidites (as shown in FIGS. 3 and 4) are compatible with oligonucleotide syntheses. Accordingly many embodiments are directed to methods of forming PDI phosphoramidites using automated synthesizers, and allows for polymerization of PDI derivatives in a controlled manner, such that the length, sequence and terminal functionality can be designed (See FIGS. 6A, 6B, and 7). Determination of length, sequence, and terminal functionality may be dependent on the intended use the PDI polymer. For example, molecular wires may be designed to have a precise length necessary for an application (e.g., nanowires).

Figure 7:
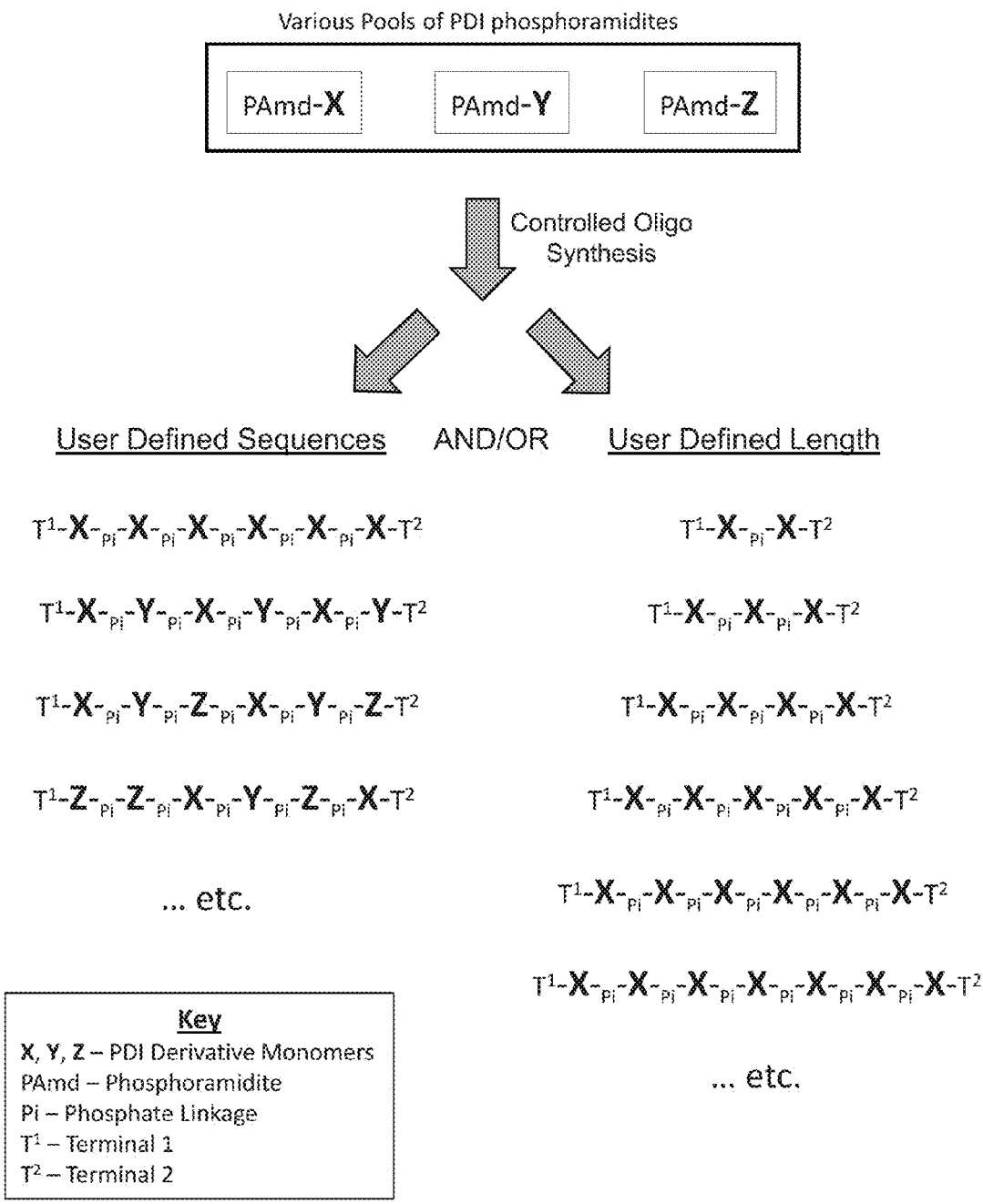
FIG. 7 provides a schematic diagram of a process to control PDI polymer sequence, length, and termini using various PDI phosphoramidites as building blocks, in accordance of various embodiments of the invention.
Figure 8:
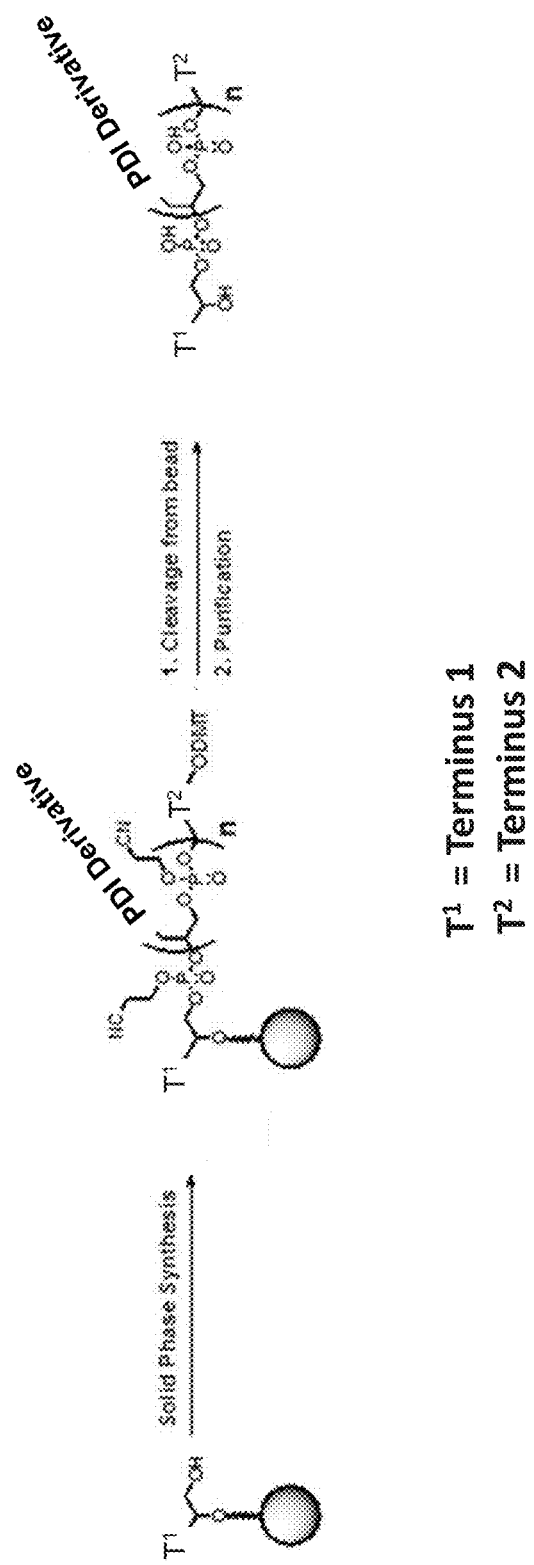
FIG. 8 provides a schematic diagram for molecular wire synthesis on a solid phase, in accordance with various embodiments of the invention.
Figure 9:
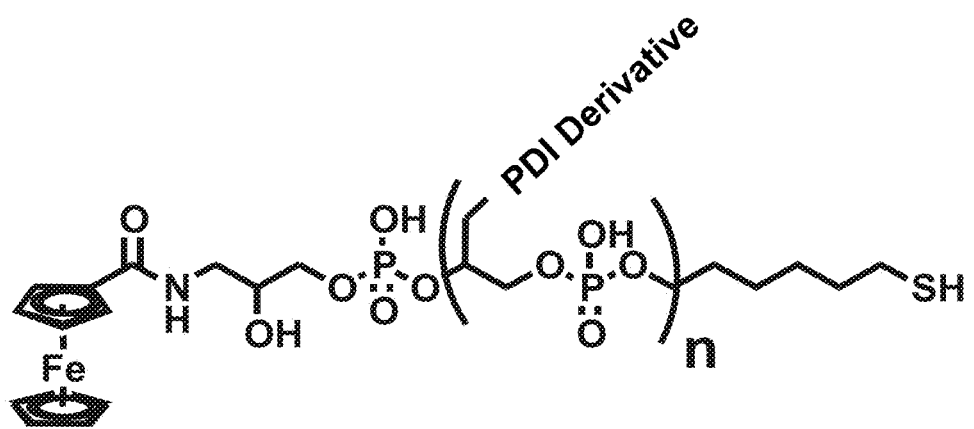
FIG. 9 provides a molecular diagram of PDI polymers linked via phosphates flanked with thiol functionalized terminus and ferrocene functionalized terminus, in accordance with various embodiments of the invention.

In a number of embodiments, the PDI polymer sequence can be controlled during the polymerization process, such as when synthesized using an automated oligonucleotide synthesizer (FIG. 7). Accordingly, an individual can design the PDI to a precise sequence and length, building PDI polymers by iterative linking of PDI phosphoramidites. PDI polymers can be assembled using various nucleic acid synthetic polymerization techniques, which are well known in the field (See FIG. 8). Typically, monomers are iteratively added to a polymer on a solid support by a protective process to ensure a single monomer is added in each step. Because an individual can control which monomers are added at each iteration and the number of iterations to be performed, one can design and synthesize a PDI polymer with ultimate precision. In addition, oligosynthesizers can be programmed to perform the iterative polymerization in an automated fashion. After completion of polymerization, a PDI polymer may be cleaved from the solid support and purified by any known methods in field, yielding a designed polymer (FIG. 8).

The use of iterative PDI polymerization techniques can yield a number of designer polymers. Accordingly, various embodiments are directed to phosphate-linked polymers having a single repeat PDI derivative monomer. In other embodiments, at least two different PDI derivatives incorporated into the polymer. Further embodiments are directed to designer sequences of multiple PDI derivatives, which may have desired chemical or electrical properties for a particular application or functionality. It should be noted that although FIG. 7 only depicts three PDI derivatives, but it should be understood that any number of PDI derivatives can be used, depending on the use and application of the PDI polymer.

More embodiments are directed to controlling the length of a PDI polymer (FIG. 7). In a number of embodiments, the PDI polymer is two, three, or four monomers long. In some more embodiments, the polymer length is any number chosen by the user capable of being synthesized. Current protocols used in the field can synthesize nucleic acid polymers strands of a couple hundred bases, and compiled polymers up to a couple thousand bases with sequence and length precision accuracy. Likely, polynucleotide synthesis will continue to improve over time, and thus can be incorporated into embodiments of PDI-polymerization protocols defined within, enhancing the ability to build longer phosphate-linked PDI polymers. Accordingly, embodiments are directed to PDI polymers with a precise length (i.e., precise number of monomers). In some of these embodiments, a PDI polymer strand is at least 20 monomers; in others, at least 100 monomers; and in even more, at least 200 monomers.

In various embodiments, PDI polymers may be end-capped with a variety of functional groups to be used in a variety of applications. In some embodiments, for example, an electroactive ferrocene moiety may be disposed at one terminus of strands of PDI molecules. Alternatively or in addition, a thiol may be disposed at a terminus during the programmed synthesis process. Exemplary embodiments of such terminal substitutions are shown in FIG. 8. In some such embodiments, the sulfur (e.g., thiol) moieties can be next used to, for example, anchor PDI polymers to various surfaces (e.g., gold). Other embodiments are directed to amino, hydroxyl, and carbonyl groups used as polymer termini. In several such embodiments, a terminal group functions to attach the polymer to various connectors. Embodiments of PDI polymers with ferrocene terminal function allow for electrochemical probing of the polymer itself.

Further embodiments are directed to synthesis of multiple PDI polymers at the same time, with the same precision and control for each polymer. Accordingly, embodiments are directed to a collection of PDI polymers that are monodisperse, each having the same sequence, length, termini. Although polymerization results in various yields of a designed polymer, the desired polymer may be purified to high percent yields by a number of known protocols (e.g., HPLC). In more embodiments, the collection of PDI polymers are stored in a suitable solution or lyophilized into a dried salt.

Molecular Nanowires

Molecular electronic devices have the potential to redefine integrated circuit technologies and revolutionize modern computing. (See, e.g., K. Moth-Poulsen, *Handbook of Single-Molecule Electronics*, Pan Stanford Publishing, Boca Raton, 2015; and D. M. Guldi, H. Nishihara, L. Venkataraman, *Chem. Soc. Rev.* 2015, 44, 842-844, the disclosures of which are incorporated herein by reference.) Consequently, much effort has focused on the discovery and study of nearly "lossless" molecular wires or molecular chains that efficiently transport charge. (See, e.g., G. Sedghi, et al., *Nat. Nanotech.* 2011, 6, 517-523; G. Sedghi, et al., *Adv. Mater.* 2012, 24, 653-657; W. B. Davis, et al., *Nature* 1998, 396, 60-63; H. D. Sikes, et al., *Science* 2001, 291, 1519-1523; J. D. Slinker, et al., *Nat. Chem.* 2011, 3, 228-233; and L. Xiang, et al., *Nat. Chem.* 2015, 11, 221-226 the disclosures of which are incorporated herein by reference.) However, for many of the reported molecular wires, the charge transport rate or conductivity drops off precipitously with length in the tunneling regime (typically <~5 nm). Furthermore, artificial molecular wires are often difficult to synthesize, while natural molecular wires can exhibit poor stability under electrical interrogation. (See, e.g., N. J. Tao, *Nat. Nanotech.* 2006, 1, 173-181; S. V. Aradhya, L. Venkataraman, *Nature Nanotech.* 2013, 8, 399-410; Jia, B. Ma, N. Xin, X. Guo, *Acc. Chem. Res.* 2015, 48, 2565-2575; H. Song, M. A. Reed, T. Lee, *Adv. Mater.* 2011, 23, 1583-1608; M. D. Newton, J. F. Smalley, *Phys. Chem. Chem. Phys.* 2007, 9, 555-572; A. L. Eckermann, et al., *Coord. Chem. Rev.* 2010, 254, 1769-1802; E. A. Weiss, et al., *Top. Curr. Chem.* 2005, 257, 103-133; C. Schubert, et al., *Chem. Soc. Rev.* 2015, 44, 988-998; S. S. Skourtis, *Biopolymers,* 2013, 100, 82-92; and R. J. Nichols, S. J. Higgins, *Annu. Rev. Anal. Chem.* 2015, 8, 389-417, the disclosures of which are incorporated herein by reference.) Consequently, given the continued demand for integrated circuit miniaturization, the development of high-performance molecular wires remains of paramount importance for next generation electronics. (See, e.g., M. M. Waldrop, *Nature* 2016, 530, 144-147, the disclosure of which is incorporated herein by reference.)

The availability of methods for precise assembly of molecular wires is crucial for obtaining rationally designed materials with predictable and tunable electronic properties, especially in the sub-10 nm length operational regime approached by some current transistors and bioelectronics devices. Many types of nanowires have been proposed and even fabricated, including perylene-based nanowires, however, most production efforts rely on bulk assembly techniques or poorly controlled polymerizations. Although these techniques can furnish long nanowires out of the available building blocks, the precise control over the nanowire length, sequence, or other key geometric parameters remain elusive.

Accordingly, embodiments are provided for the preparation and characterization of molecular wires from the PDI derivatives set forth herein. In many such embodiments, phosphoramidite functionalized PDI derivatives according to embodiments are used as molecular building blocks for the assembly of molecular wires, where the perylene core is the basis of the wires' self-arrangement/π-stacking and resulting electronic properties and phosphoramidite functionality ensures compatibility with oligonucleotide synthesis protocols and equipment to polymerize the nanowire via a phosphate backbone. In further embodiments, phosphoramidite functionalized PDI derivatives also contain PEG adduct to ensure solubility in either water or organic solvents. As such, the approach according to various embodiments employs entrenched nucleic acid polymer synthesis and self-assembly techniques to produce well defined arrays of columnar stacks of organic semiconductor building blocks at solid substrates, as shown schematically in FIG. 8. Such an assembly method affords exquisitely precise phosphate-linked nanowire fabrication, including incorporation of chain terminal groups of choice, which is difficult to achieve within any other traditional synthesis and self-assembly contexts.

Figure 10:
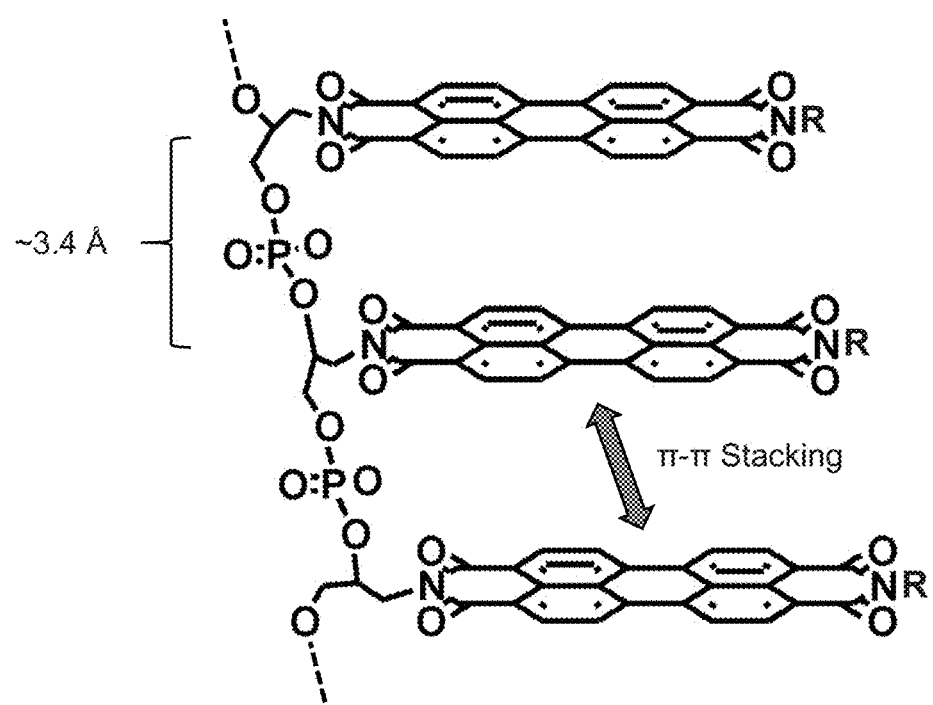
FIG. 10 provides a molecular structure diagram of a molecular wire linked via a phosphate backbone such that PDI monomers are ~3.4 Å apart and interact with neighboring PDI monomers via π-π stacking, in accordance with various embodiments of the invention.

Using such embodiments of molecular wire generation, it is possible to "lock in" the same π-π stacking interactions similar to those found in PDI crystals and the phosphate backbone will ensure a distance of ~3.4 Å between neighboring PDI monomers, similar to the distance between nucleotides in a nucleic acid polymer (See FIG. 10). Furthermore, by varying the alkyl substituents at the free imide position of the PDI monomers, it is possible to control the structural interaction of adjacent building blocks (See FIG. 10; R functionality). Embodiments of nanowires in accordance with embodiments are thus capable of using a phosphate backbone to enforce the desirable packing found in PDI crystals (See FIG. 11). In such crystals, the PDI monomers form columnar structures with intermolecular PDI distances between 3.34 and 3.55 Å, and the transverse and longitudinal offset of adjacent PDI monomers being controlled by steric interactions between the PDI imide substituents. Accordingly, in many embodiments the nanowires may be characterized as one-dimensional crystalline-like columns locked into a π-stacking conformation.

The anionic phosphate backbone according to a number of embodiments facilitates a high throughput systematic structural characterization of PDI nanowires from monomers with different imide substituents. Using commercial nucleic acid synthesis protocols, it is then possible to grow PDI nanowires having crystalline-like columns. In some embodiments the relative orientation of the PDI monomers may be determined via crystallochromy (color changes resulting from the interaction of the 7-conjugated systems in a solid-state lattice). (See, e.g., Kazmaier, P. M.; Hoffman, R. J. Am. Chem. Soc. 1994, 116, 9684-9691; and Herbst, W.; Hunger, K. Industrial Organic Pigments: Production, Properties, Applications, 2nd ed. Wiley: Weinheim, 1997, the disclosure of which is incorporated herein by reference.)

Figure 11:
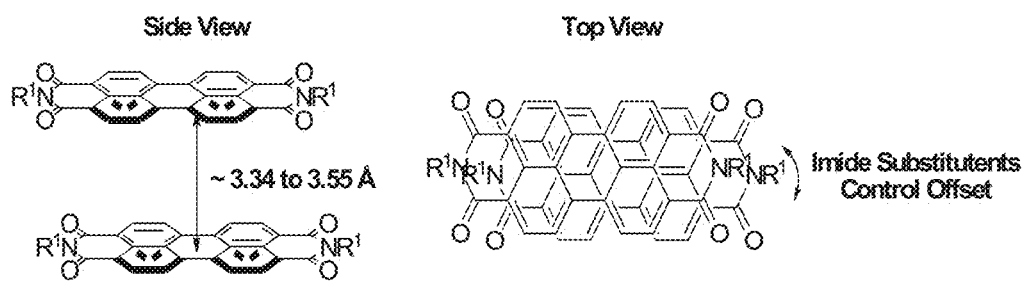
FIG. 11 provides molecular structure diagrams of two possible π-π stacking motifs for molecular wires in the solid state, where the choice of the imide substituents controls the π-π contact area and the color of the PDI crystals, in accordance with various embodiments of the invention.
Figure 11:
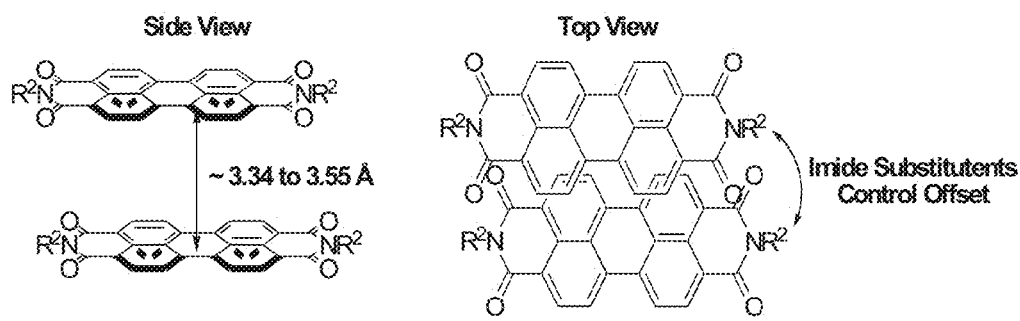

Indeed, the bathochromic shift and band broadening found for the absorbance of PDI dyes in the solid state can be quantitatively and empirically related to the π-π contact area between the stacked chromophores; red coloration indicates a small contact area and black coloration indicates a large contact area (see, e.g., FIG. 11). Using crystallochromic studies it is possible to rapidly screen for nanowires where neighboring PDI monomers that have a minimal offset and assume a cofacial configuration; this type of stacking favors excellent charge transport properties in organic materials (as discussed in the Exemplary Embodiments).

Using the techniques, according to embodiments, it is possible to form organic nanowires with varying lengths and compositions by incorporating different numbers of distinct PDI building blocks. In many embodiments, automated oligosynthesis may be used to form organic nanowires with controlled lengths (e.g., between ~10 nm and ~50 nm; ~30 to ~150 monomer units) to a precision that is incapable of being obtained using standard organic nanowire engineering. It is also possible to precisely control the placement and environment of every single PDI building block by modulating the "sequence context" of the nanowire. For example, it is possible to synthesize nanowires where a short tract of one type of PDI is embedded between two longer tracts of another type of PDI. In addition, it is possible to synthesize nanowires where the two types of PDI monomers are intermixed (See FIG. 7). Using such techniques it is possible to rationally tune both the local and global electronic properties of the organic nanowires, which will be crucial for subsequent electrical and electrochemical studies.

Accordingly, anionic phosphate backbones according to embodiments allow for the processing of the PDI polymer nanowires under aqueous (or partially aqueous) conditions. It is therefore possible to purify the PDI polymer nanowires via high performance liquid chromatography (HPLC), a technique that typically yields DNA products with >99.9% purity and a polydispersity of 1.0. This ease of purification allows for the production of the first ex situ synthesis of long, well-defined, and monodisperse organic nanowires with lengths >~40 nm. Embodiments of the compounds and synthetic methods furnish water soluble, low-resistance, organic nanowires for the next generation of high performance miniaturized electronics (OLEDs, OPVs, OFETs, etc.). Moreover, the described nanowire assembly method, which is a standard automated oligonucleotide chemistry technique, uses highly modular, photo- and electroactive building blocks, and allows for precise control of chain length, composition, and user-specified terminal functionality. Furthermore, the assembly products' good solubility in a variety of solvents, including water, enables facile processing with established industrial techniques, including DNA purification and deposition techniques. In addition, the accessible modularity of the building blocks ensures that the physical properties of the whole system can be tuned for an array of applications. Finally, the easy installation of terminal substituents warrants the materials' convenient post-synthetic assembly into devices.

Embodiments of nanowires having various derivatives of PDI molecules can be utilized in a number of electronic devices and applications, including organic field-effect transistors (OFETs), electrophotographic devices, and organic photovoltaic cells (OPVs). PDIs are good molecules for use as the attractive layer of n-channel field effect transistors due to their relatively exergonic electron affinities. In a number of embodiments, nanowires have facile electron injection and low threshold voltages. More embodiments are directed to nanowires with high charge-carrier mobilities.

The use of molecular organic wires may have several benefits, including lossless charge transport. In many embodiments, electrons are transported through the macromolecules' tethers and linkers via a rate-limiting and loosely non-resonant tunneling mechanism. Further embodiments are directed to electrons that are transported through the macromolecules' PDI-based substructures via a rapid and nearly lossless resonant tunneling mechanism. The combination of these two mechanisms results in essentially length-independent charge transport for embodiments of the constructs, in accordance with several embodiments.

EXEMPLARY EMBODIMENTS

Many embodiments are also directed to methods of synthesizing PDI molecules and derivatives, PDI polymers, and molecular nanowires therefrom. Although specific reagents and methodologies are described in the embodiments that follow, it will be understood that these procedures are included for exemplary purposes and the scope of the synthetic methods of synthesis are not intended to be limited thereto.

Example 1: Synthesis of PDI Derivatives

Materials:

All general chemical reagents were purchased from Acros Organics, Sigma-Aldrich, or Combi-Blocks. The solvents were obtained from Fisher Scientific and used as received, unless otherwise noted. Flash chromatography was performed using SiliCycle Silica Flash F60 silica gel. The specific chemical reagents and commercial phosphoramidites required for the automated synthesis steps were purchased from either Glen Research, Inc. or FIVEphoton Biochemicals, Inc. and used as received.

General Procedures for Characterization of the Small Molecule Precursors:

All intermediates and products for the phosphoramidite synthesis were characterized with nuclear magnetic resonance (NMR) spectroscopy and mass spectrometry. The electrospray mass spectrometry (ESI MS) data were obtained at the University of California, Irvine Mass Spectrometry Facility on a Waters LCT Premier Electrospray time-of-flight instrument. The $^{1}H$ NMR spectra were obtained on either a Bruker DRX500 or an AVANCE600 instrument. The $^{13}C$ NMR spectra were obtained on a Bruker DRX500 outfitted with a CryoProbe (Bruker TCI 500 MHz, 5 mm diameter tubes). The $^{31}P$ NMR spectra were acquired on a Bruker AVANCE600 instrument. Chemical shifts were reported in ppm for $^{1}H$, $^{13}C$, $^{19}F$, and $^{31}P$ NMR. The chemical shifts for the NMR data were referenced as follows: for samples in $CDCl_3$, the $^{1}H$ NMR was referenced to tetramethylsilane (TMS) at 0.00, and the $^{13}C$ NMR was referenced to $CDCl_3$ at 77.23; for samples in $CD_3OD$, the $^{13}C$ NMR was referenced to the solvent peak at 49.00; for samples in $CD_2Cl_2$, the $^{1}H$ NMR was referenced to the solvent peak at 5.32, and the $^{13}C$ NMR was referenced to the solvent peak at 54.00. The chemical shifts for the $^{31}P$ NMR spectra were corrected and referenced by using $^{1}H$ NMR according to the 2008 IUPAC recommendations. The data are labeled as follows: chemical shift, multiplicity (s=singlet, d=doublet, t=triplet, q=quartet, quint=quintet, m=multiplet, br s=broad singlet), the coupling constants (in Hertz), and the integration value.

Phosphoramidite Synthetic Protocols:

The following exemplary synthetic protocols will be described in relation to FIG. 12.

(S)-3-trifluoroacetamido-1,2-propanediol (S1)

Figure 12:
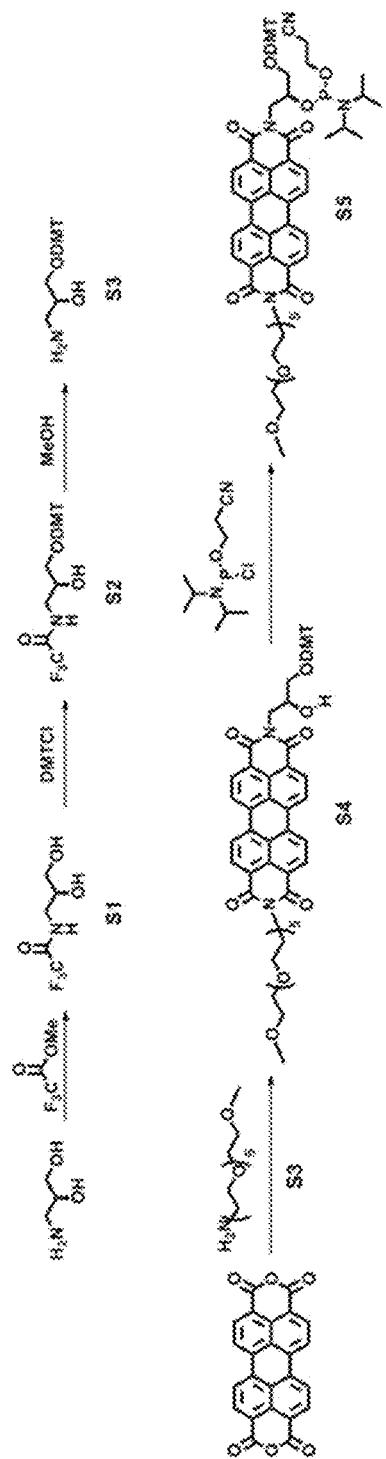
FIG. 12 provides a synthetic schematic diagram for synthesis of PDI phosphoramidites in accordance with various embodiments of the invention.

Product S1 in FIG. 12 was synthesized according to established literature protocols. (See, e.g., A. V. Azhayev, M. L. Antopolsky, Tetrahedron 2001, 57, 4977-4986; and C. Wagner, H.-A. Wagenknecht, Org. Lett. 2006, 8, 4191-4194, the disclosures of which are incorporated herein by reference.)

(S)-3-trifluoroacetamido-1-(4,4'-dimethoxytriphenyl-methyl)-2-propanediol

Product S2 in FIG. 12 was synthesized according to established literature protocols. (See, e.g., A. V. Azhayev, M. L. Antopolsky, Tetrahedron 2001, 57, 4977-4986; and C. Wagner, H.-A. Wagenknecht, Org. Lett. 2006, 8, 4191-4194, the disclosures of which are incorporated herein by reference.)

(S)-3-amino-1-(4,4'-dimethoxytriphenylmethyl)-2-propanediol (S3).

Product S3 in FIG. 12 was synthesized according to established literature protocols. (See, e.g., A. V. Azhayev, M. L. Antopolsky, Tetrahedron 2001, 57, 4977-4986; and C. Wagner, H.-A. Wagenknecht, Org. Lett. 2006, 8, 4191-4194, the disclosures of which are incorporated herein by reference.)

Precursor for the Perylene Diimide Phosphoramidite (S4).

Product S4 in FIG. 12 was synthesized according to a procedure adopted from the literature. (See, e.g., C. H. Wohlgamuth, et al., J. Phys. Chem. C 2014, 118, 29084-29090; C. B. Markegard, et al., J. Phys. Chem. B2015, 119, 11459-11465; and C. Wagner, H.-A. Wagenknecht, Org. Lett. 2006, 8, 4191-4194, the disclosures of which are incorporated herein by reference.) First, 0.741 g (1.91 mmol, 1.0 equiv) of 3,4,9,10-perylenetetracarboxylic dianhydride and 0.713 g (3.89 mmol, 2.0 equiv) of anhydrous $Zn(OAc)_2$ were combined in an oven-dried round bottom flask. Anhydrous pyridine (17 mL) was then added via syringe, and the flask was fitted with a water-cooled condenser. The mixture was heated to reflux, and after 1.5 h, a solution of 2,5,8,11,14,17-hexaoxanonadecan-19-amine (0.568 g, 1.92 mmol, 1.0 equiv) in 10 mL of anhydrous pyridine and a solution of (S)-3-amino-1-(4,4'-dimethoxytriphenylmethyl)-2-propanediol (0.755 g, 1.92 mmol, 1.0 equiv) in 10 mL anhydrous pyridine were successively added to the flask. The resulting mixture was stirred rapidly and maintained at reflux for ~22 hours under argon. The reaction was subsequently allowed to cool to room temperature, concentrated to ~1/10 of the original volume by rotary evaporation, diluted in $CH_2Cl_2$ (150 mL), and poured into a separatory funnel. The crude mixture was extracted with aqueous KOH (1 M, 3×150 mL), dried for 5 min over anhydrous $Na_2SO_4$, and filtered. Next, silica gel (8 mL) was added to the crude product solution, and the solvent was removed by rotary evaporation. The resulting material was loaded in its dry state onto a silica gel column (245 mL silica gel, 5.5 cm O.D. column), and the products were eluted with $CH_2Cl_2$:methanol (from 99:1 to 85:15 in 3000 mL total eluent). The procedure yielded 820 mg (41%) of product S4 as a dark red solid.

Perylene Diimide Phosphoramidite (S5)

Product S5 in FIG. 12 was synthesized according to a procedure adopted from the literature. (See, e.g., C. H.

Wohlgamuth, et al., *J. Phys. Chem. C* 2014, 118, 29084-29090; C. B. Markegard, et al., *J. Phys. Chem. B* 2015, 119, 11459-11465; and C. Wagner, H.-A. Wagenknecht, *Org. Lett.* 2006, 8, 4191-4194, the disclosures of which are incorporated herein by reference.) First, 0.4 g (0.383 mmol, 1.0 equiv) of the perylene diimide precursor (S4), dichloromethane (4 mL), and distilled triethylamine (0.27 mL, 1.91 mmol, 5 equiv) were added to a scintillation vial under nitrogen. Once S4 had dissolved to produce an opaque red solution, 0.085 mL of N,N-diisopropylamino-β-cyanoethyl chlorophosphoramidite (0.381 mmol, 0.99 equiv) was added via syringe. After stirring for 3 hours, the solution was poured into a separatory funnel, rinsed and diluted with sparged $CH_2Cl_2$ (3×4 mL), and extracted with sparged aqueous $NaHCO_3$ (saturated, 3×10 mL). The organic phase was dried for 1 min over $Na_2SO_4$, filtered, and concentrated by rotary evaporation/vacuum drying to yield 438 mg (92%) of product S5 as a dark red solid. This product contained a mixture of diastereomers.

Example 2: Synthesis and Characterization of Molecular Wires

Figure 13:
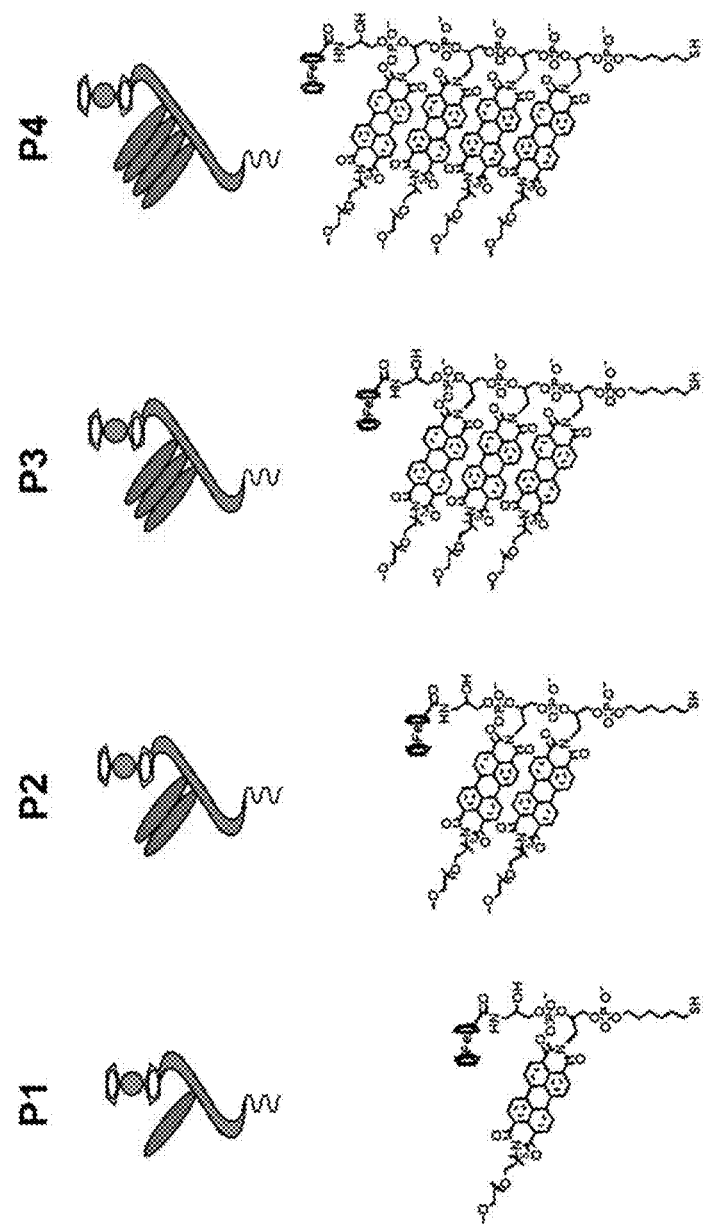
FIG. 13 provides a schematic Illustration (top) and chemical structure (bottom) for exemplary macromolecules, which consist of tracts of one to four PTCDIs arranged on a phospho-alkane backbone and flanked by thiol-terminated linkers and ferrocene-terminated tethers, denoted as P1, P2, P3, and P4, generated in accordance of various embodiments of the invention.
Figure 14:
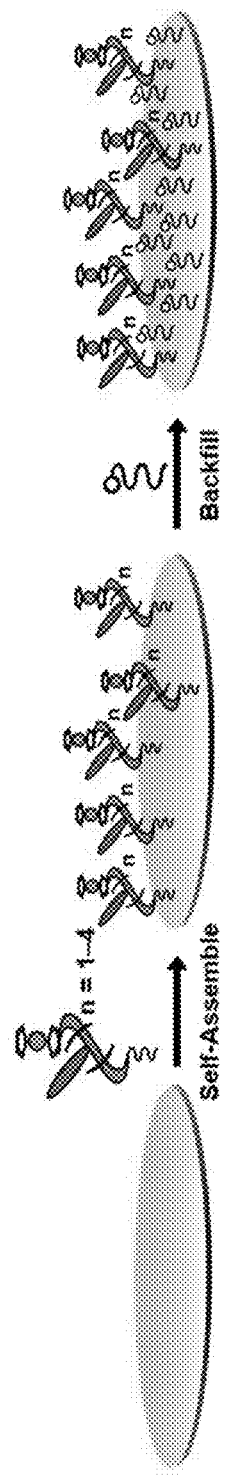
FIG. 14 provides an illustration of self-assembled monolayer formation for the macromolecules generated in FIG. 13, used in accordance of various embodiments of the invention.
Figure 15:
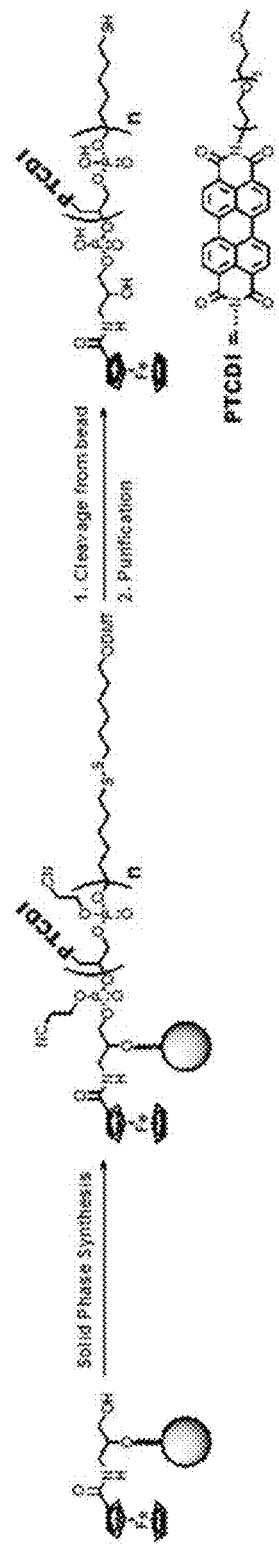
FIG. 15 provides a synthetic schematic diagram, which can be performed in an automated oligosynthesizer, for the iterative polymerization of the macromolecules in FIG. 13, applied in accordance of various embodiments of the invention.
Figure 16:
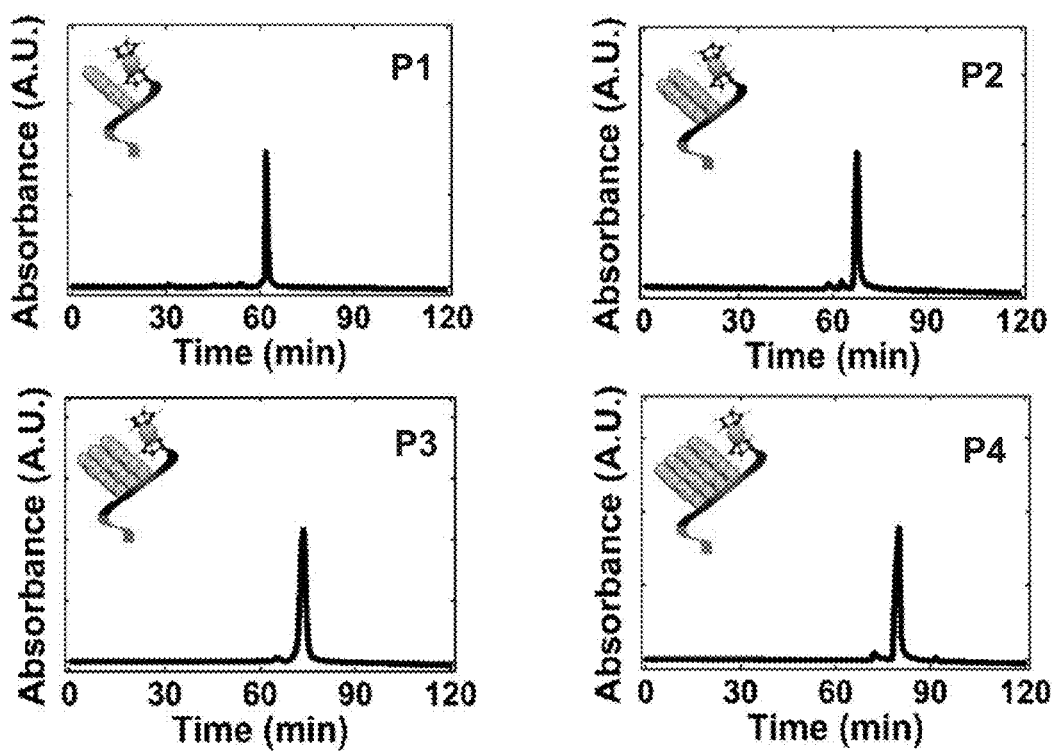
FIG. 16 provides data plots of HPLC chromatograms for macromolecules P1, P2, P3, and P4, generated in accordance with various embodiments of the invention.
Figure 17:
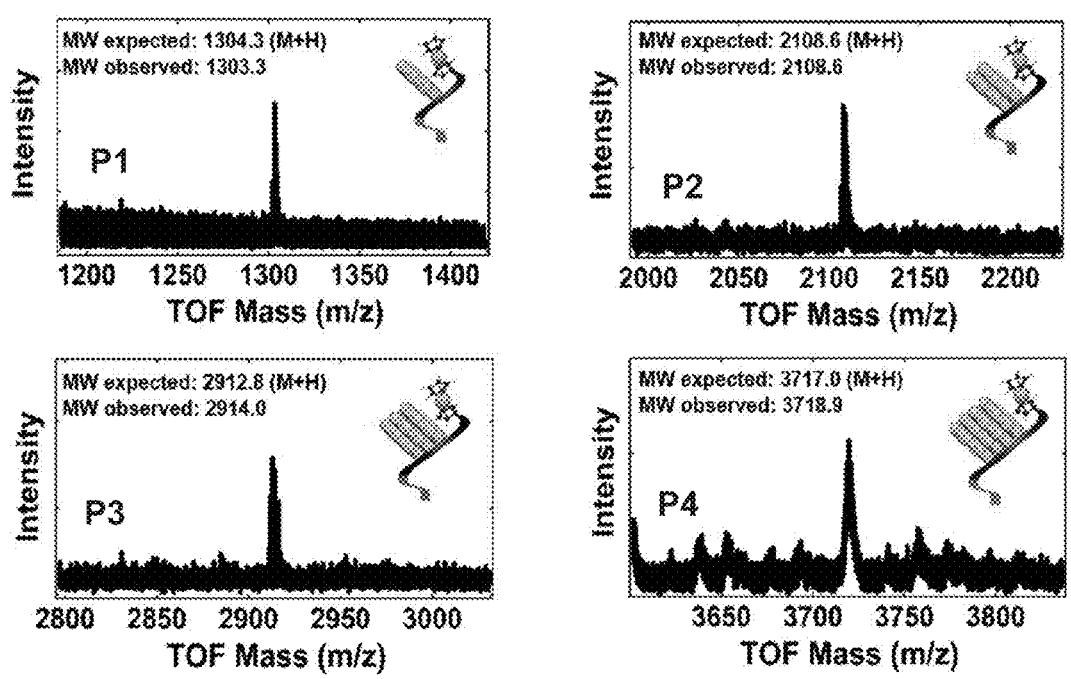
FIG. 17 provides data plots of MALDI-TOF spectra for macromolecules P1, P2, P3, and P4, generated in accordance with various embodiments of the invention.

Macromolecules (e.g., P1, P2, P3, and P4 from FIG. 13) were synthesized on solid support (as shown in FIG. 14) according to standard commercial protocols recommended by Glen Research, Inc. for an Applied Biosystems (ABI) 394 DNA synthesizer (See, e.g., FIG. 15). The synthesis cycle was modified to omit the capping step and to use extended coupling times for the incorporation of both the thiol modifier C6 S—S phosphoramidites and perylene diimide phosphoramidites, as previously described. (See, e.g., C. H. Wohlgamuth, et al. J. Phys. Chem. C 2014, 118, 29084-29090; and C. B. Markegard, et al., J. Phys. Chem. B 2015, 119, 11459-11465, the disclosures of which are incorporated herein by reference.) After synthesis, the macromolecules were cleaved from the support by treatment with aqueous ammonium hydroxide and purified via reverse phase high performance liquid chromatography (HPLC) on an Agilent 1260 Infinity system, equipped with an Infinity Series diode array detector. Macromolecules P1, P2, P3, and P4 were eluted with a gradient evolved from 40% solvent A and 60% solvent B to 0% solvent A and 100% solvent B over 120 min at a flow rate of 1 mL/min (solvent A, 50 mM ammonium acetate, pH=6 buffer; solvent B, methanol) on Agilent ZORBAX Stable Bond Phenyl columns (see, e.g., FIG. 16 for representative chromatograms). The MALDI-TOF mass spectra of the macromolecules were obtained on an Applied Biosystems Sciex MALDI-TOF/TOF 5800 series mass spectrometer in reflectron negative mode, using a 349 nm Nd:YAG laser as the illumination source (see, e.g., FIG. 17 for representative spectra).

Self-Assembly of the Mixed Monolayers

Monolayers from macromolecules P1, P2, P3, and P4 were formed on 80 nm gold films evaporated onto Si substrates (International Wafer Service, Inc.). Prior to monolayer assembly, the films were cleaned with sequential sonication in acetone, isopropanol, and methanol. The macromolecules were self-assembled from methanol over a period of 16 to 24 hours. The monolayers were in turn backfilled with 1 mM mercaptohexanol, displacing non-specifically bound macromolecules. The PTCDI multilayers were prepared by dropcasting PTCDI onto gold-coated Si substrates. The monolayers and multilayers were used for spectroscopic measurements immediately after preparation.

X-Ray Spectroscopy of the PTCDI-Based Monolayers and Multilayers.

X-ray spectroscopy experiments were performed at the ALOISA beamline of the Elettra Synchrotron in Trieste, Italy in an ultra-high vacuum end station. During the experiments, the sample temperature was maintained at −60° C., and the measurement and sample preparation chamber pressures were maintained at $10^{-11}$ mbar and $10^{-10}$ mbar, respectively. The backfilled monolayers and multilayers were characterized using resonant photoemission spectroscopy (RPES). The RPES experiments were performed by taking XPS scans (0 to 50 eV binding energy, $E_p$=40 eV) at a series of incident photon energies across the entire range of the carbon K-edge ionization threshold (278 eV to 310 eV). The surface was oriented at a grazing-incidence angle of 4° and in P-polarization, with a hemispherical electron analyzer positioned at 55° from the surface normal at an acceptance angle of 2°. The data obtained for all of the measurements was analyzed and processed according to established literature procedures. (See, e.g., P. A. Brühwiler, et al., Rev. Mod. Phys., 2002, 74, 703; O. Björneholm, et al., □Phys. Rev. Lett., 1992, 68, 1892; M. Ohno, Phys. Rev. B, 1994, 50, 2566; O. Karis, et al., Phys. Rev. Lett., 1996, 76, 1380; P. Vilmercati, et al., Surf. Sci., 2009, 603, 1542; L. Cao, et al., Adv. Mater., 2014, 26, 7880; A. Batra, et al., Nat. Comm., 2012, 3, 1038; T. Schiros, et al., Adv. Energy Mater., 2013, 3, 894; L. Cao, et al., J. Phys. Chem. C, 2014, 118, 4160; L. Cao, et al., J. Chem. Phys., 2011, 135, 174701; and G. Fratesi et al., Phys. Chem. Chem. Phys., 2014, 16, 14834, the disclosures of which are incorporated herein by reference.)

Example 3: Charge Transfer Dynamics Studies

Synchrotron-based spectroscopy was used to quantify excited-state charge transfer dynamics at model organic-inorganic interfaces. A series of well-defined, backfilled monolayers via self-assembly of distinct phosphate-linked macromolecules from perylene-3,4,9,10-tetracarboxylic diimide building blocks. Next the monolayers were probed with resonant photoemission spectroscopy (RPES) and use the core-hole clock (CHC) method to quantify the rate of excited-state charge transfer, i.e. electron delocalization, from the molecules to their surroundings. An unexpected length-independent trend for the charge transfer times was observed, which may be explained with density functional theory calculations.

Figure 18:
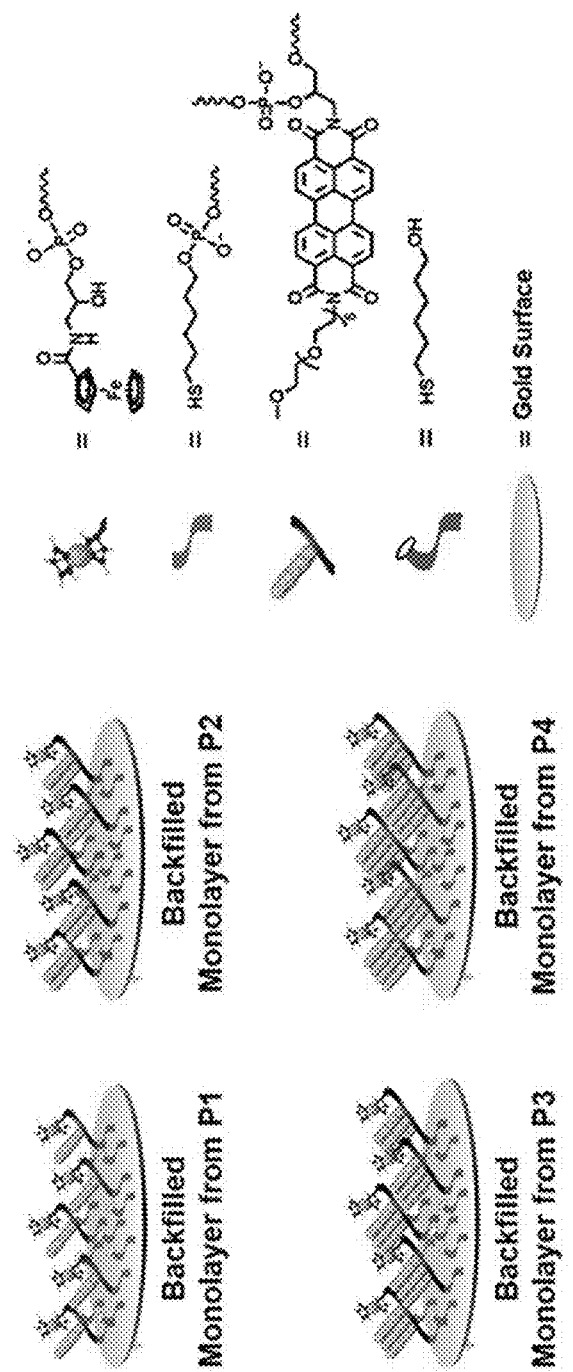
FIG. 18 provides a schematic diagrams of backfilled monolayers from macromolecules P1, P2, P3, and P4 on gold substrates, generated in accordance with various embodiments of the invention.

First, model organic-inorganic interfaces illustrated in FIG. 18, incorporating embodiments of the PDI compounds because of their promising electronic properties and self-assembly characteristics, were prepared. Next, automated oligonucleotide chemistry was used to synthesize and characterize a series of polymer macromolecules (denoted as P1, P2, P3, and P4), which consisted of one to four of the PDI moieties arranged on an alkane phosphodiester backbone, as well as alkanethiol and ferrocene functionalities at opposing. In turn, standard DNA self-assembly strategies were used to form backfilled monolayers on gold substrates from embodiments of the thiol-modified macromolecules. Importantly, the monolayers featured relatively dilute surface coverages of ~20 to ~25 pmol/cm$^2$, with the constituent PDI-based substructures adopting an upright orientation at an angle of ~60° relative to the substrate surface. Such precisely-defined organic-inorganic interfaces enables the systematic investigation and direct comparison of excited-state charge transport phenomena within a uniform context.

Figure 19:
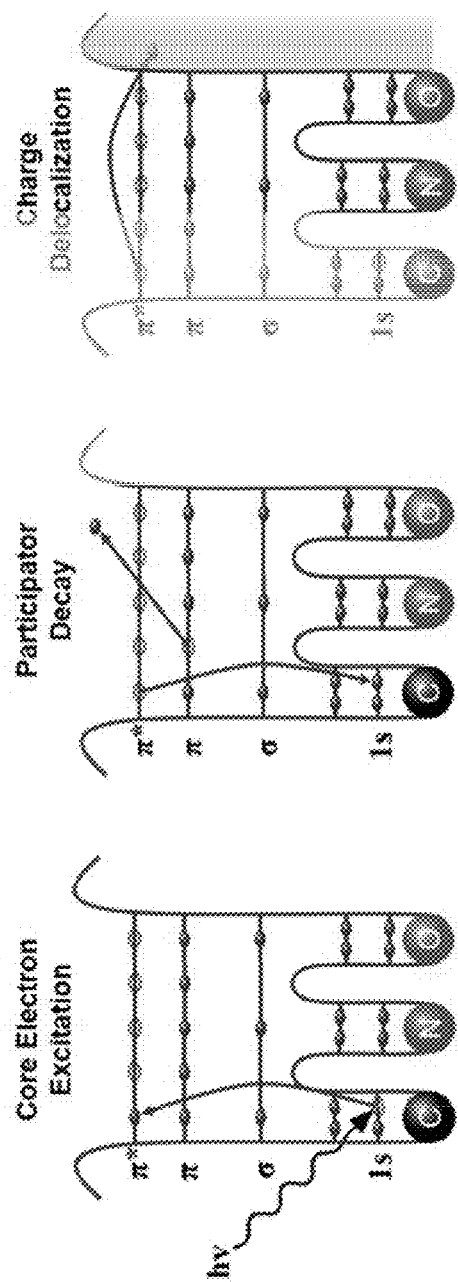
FIG. 19 provides an Illustration of the promotion of a core electron to the LUMO (left), the relaxation of the excited electron via the participator decay process (middle), and delocalization of the electron into the surrounding electronic environment (right), generated in accordance with various embodiments of the invention.
Figure 20:
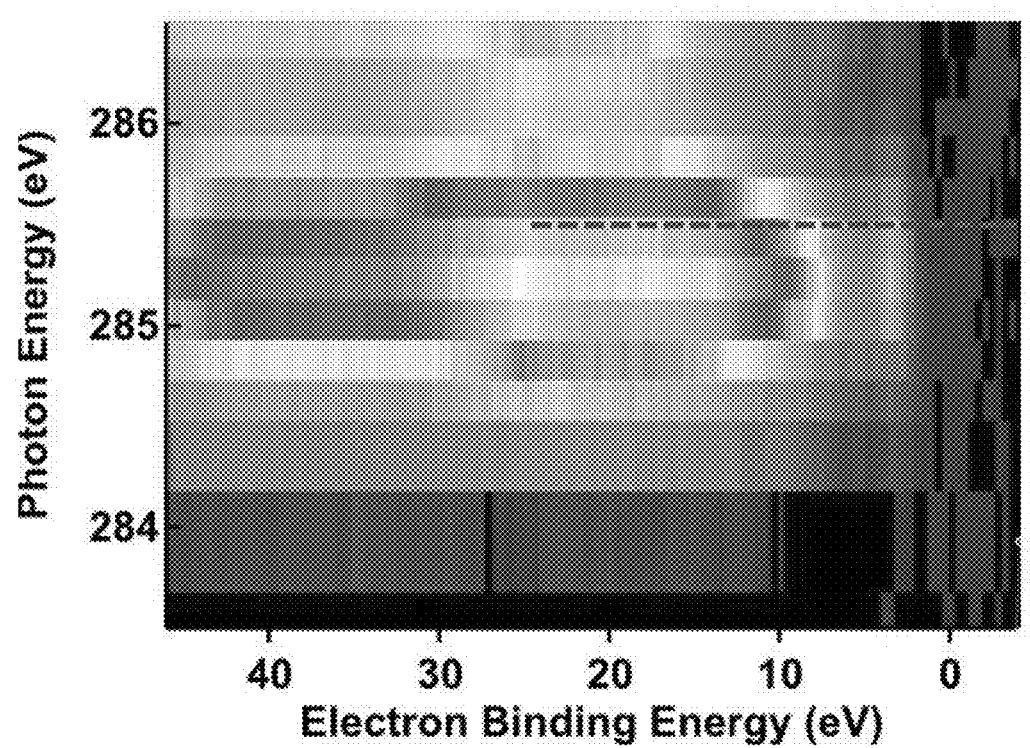
FIG. 20 provides a two-dimensional plot of the RPES intensity versus the photon energy and electron binding energy for a monolayer from P1, where the red dashed line corresponds to the one-dimensional (single photon energy) scan plot of the RPES intensity versus the electron binding energy for P1 plotted in FIG. 22, generated in accordance of various embodiments of the invention.
Figure 21A:
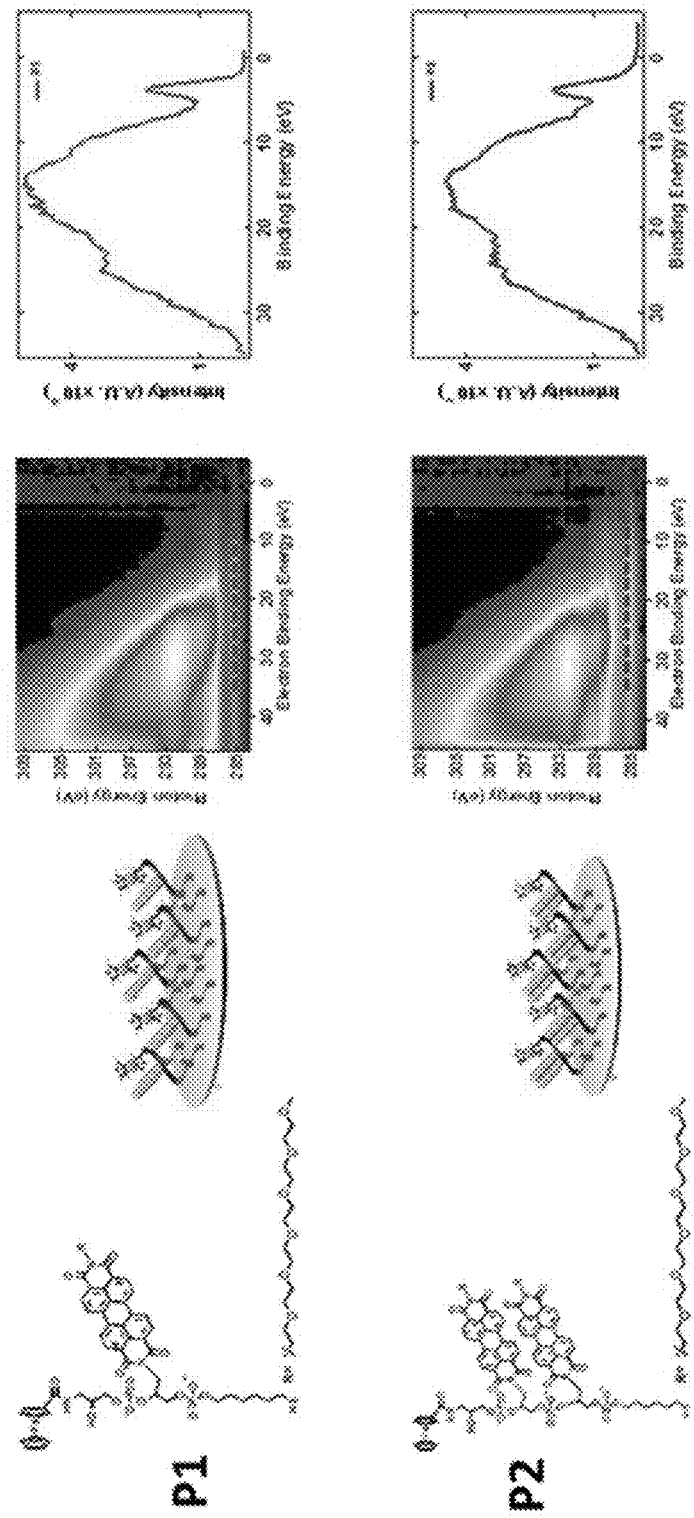
FIGS. 21A and 21B provide molecular structure diagrams of the macromolecules P1, P2, P3, and P4 (left column); illustrations of a mixed monolayer of P1, P2, P3, and P4 (middle-left column); two-dimensional plots of the signal intensity versus the photon energy and electron binding energy for a monolayer from each P1, P2, P3, and P4 where the red dashed line corresponds to the one-dimensional plot of the signal intensity versus the electron binding energy (middle-right column); and normalized resonant participator intensity profiles for each P1, P2, P3, and P4 monolayers at an incident photon energy of 285.4 eV, generated in accordance with various embodiments of the invention.
Figure 21B:
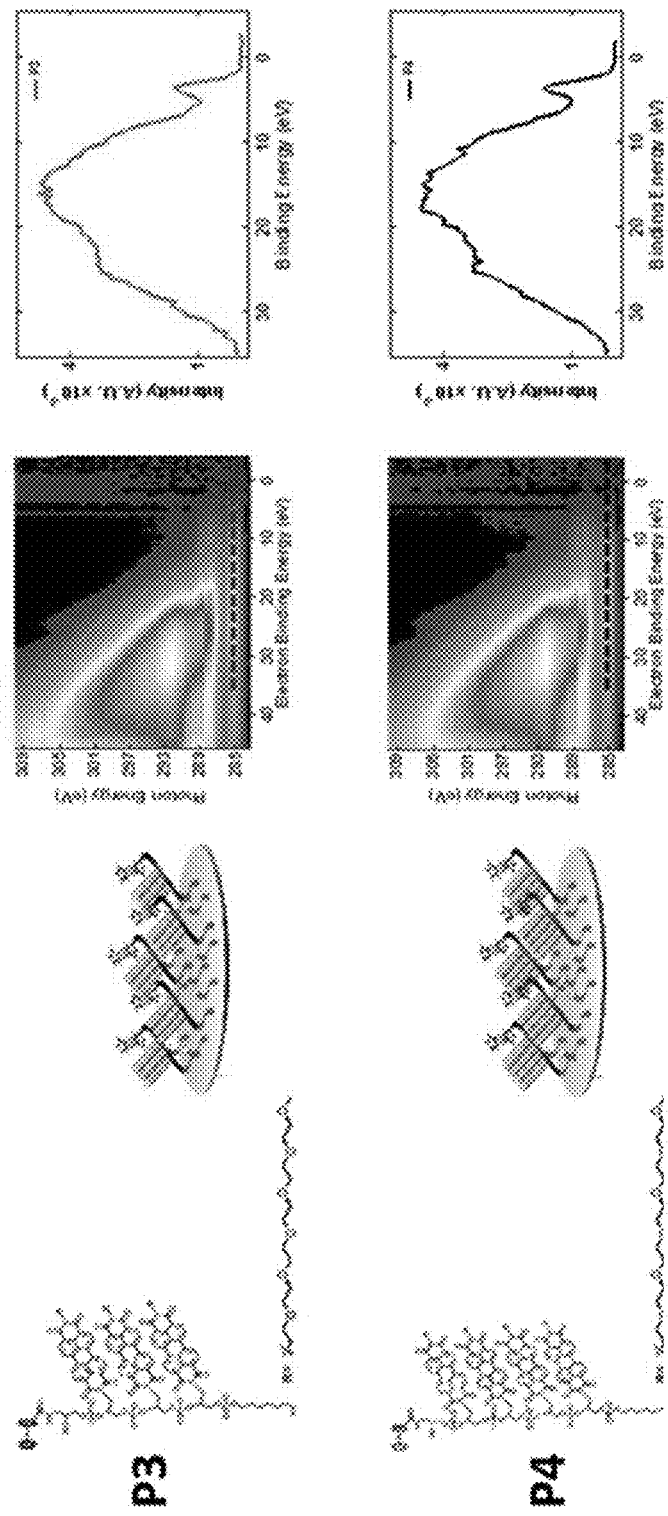

A study was undertaken on the excited-state charge transfer dynamics at the model organic-inorganic interfaces with synchrotron-based resonant photoemission spectroscopy (RPES), a surface-sensitive technique that provides information on electron delocalization with atomic-level chemical resolution and femtosecond (or even sub-femtosecond) temporal resolution. In a typical incarnation of this technique, X-ray radiation promotes an atomically localized core electron to an unoccupied orbital (e.g., the LUMO), producing an excited electron and a core-hole (FIG. 19, left). Subsequently, the excited electron may relax via multiple processes, including an autoionization process known as participator decay (FIG. 19, middle) and general charge transfer into the surroundings (FIG. 19, right). For the participator decay process, the excited electron participates in the core-hole decay and another electron from an occupied orbital (e.g. the HOMO) is ejected (FIG. 19, middle), yielding a resonantly enhanced peak that is degenerate with the direct photoemission process. For the charge transfer process, the core-excited electron delocalizes from the macromolecules' LUMO into the substrate or general surrounding electronic environment (FIG. 19, right), quenching the intensity of the participator decay signal. As a specific example, FIG. 20 shows a two-dimensional plot of the normalized resonant photoemission intensity versus the photon energy and electron binding energy for a monolayer from P1, with the non-resonant background subtracted. The plot displays a prominent peak for photon energies between 284 eV and 286 eV and binding energies between 2.2 eV to 5 eV, along with a broad Auger decay hump at higher binding energies (FIG. 20). Based on the NEXAFS and RPES spectra previously reported for PDIs, we attributed the prominent peak to the resonantly enhanced HOMO resulting from participator decay of a carbon 1s core electron that had been promoted to the LUMO and/or LUMO+1. Importantly, an analysis of the spectra obtained for monolayers from P2, P3, and P4 yielded very similar characteristic signals, which were assigned in analogous fashion (FIG. 21). These findings demonstrated that the RPES spectra of monolayers from P1, P2, P3, and P4 generally resembled both one another and the spectra previously reported for PDI-based materials.

Figure 22:
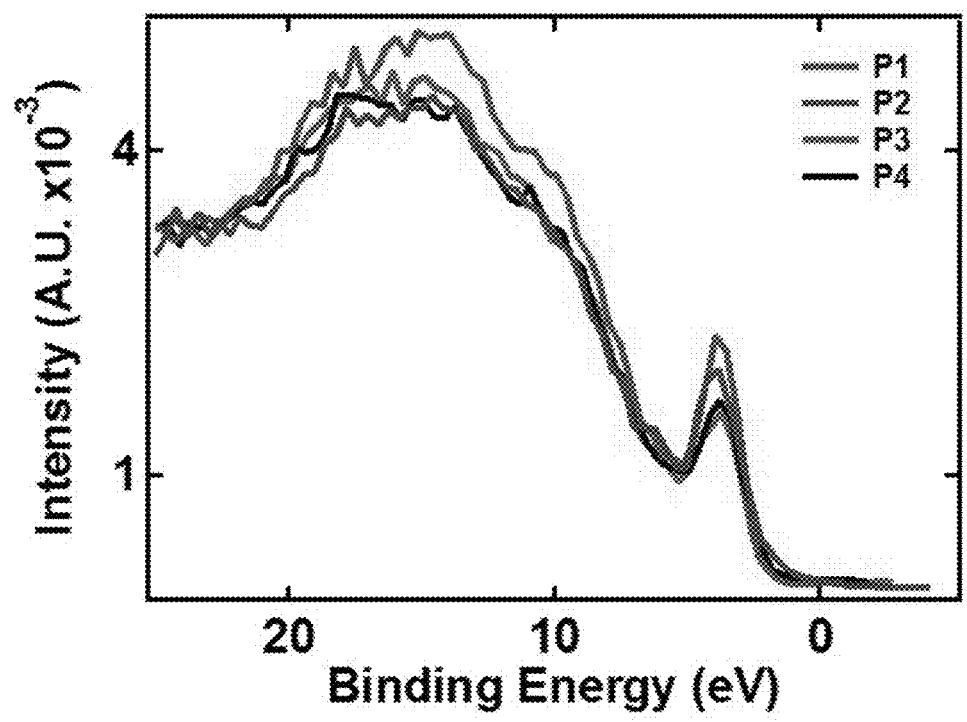
FIG. 22 provides normalized RPES intensity profiles for the P1 (red), P2 (blue), P3 (green), P4 (black) monolayers, where the data is extracted from the two-dimensional RPES intensity plots at photon energies of 285.4 eV, corresponding to the promotion of a carbon 1s core electron to the LUMO+1, generated in accordance with various embodiments of the invention.

Next, the core-hole clock method was used to evaluate the intrinsic excited-state charge transfer times from the RPES plots obtained for backfilled monolayers from P1, P2, P3, and P4. FIG. 22 shows one-dimensional plots of the RPES intensity versus the electron binding energy for these monolayers at a photon excitation energy of 285.4 eV (specifically corresponding to the promotion of a carbon 1s core electron to the LUMO+1). By evaluating the quenching of the prominent participator decay peaks at 3.4 eV, it was possible to extract the excited electron delocalization rates and hence the associated charge transfer times of 11.5±1.5 fs, 8.4±1.0 fs, 5.2±0.5 fs, and 5.7±0.6 fs for backfilled monolayers from P1, P2, P3, and P4, respectively (See FIG. 23).

The charge transfer dissociation times $\tau_{CT}$ for macromolecules P1, P2, P3, and P4 were calculated according to established literature protocols. First, the photoemission intensity at energies below the C1s-LUMO excitation (the pre-edge) was subtracted from each of the corresponding 2D RPES plots. Then, line profiles at photon energies of 285.4 eV were extracted from the 2D spectra, yielding corresponding 1D spectra and facilitating direct comparisons between the resonant spectra at the C1s→LUMO+1 transition for monolayers from P1, P2, P3, and P4. Next, the inelastic electron emission was modeled as a Shirley-type background and subtracted from each of the 1D spectra. Subsequently, the resonant spectra for the monolayers were normalized to the overall Auger intensity, enabling an analysis of the HOMO participator decay intensity quenching (See FIG. 21). The participator intensities (Ip) of the valence band resonances for P1, P2, P3, and P4 were then evaluated by integrating the peaks at a binding energy of 3.4 eV (i.e. the position of the HOMO peak), and the corresponding charge delocalization times were calculated by following the core-hole-clock approach via the equation:

$$\tau_{CT} = \tau_{CH} \frac{I_{coupled}}{I_{isolated} - I_{coupled}} \quad \text{(EQ. 1)}$$

where $\tau_{CH}$=6 fs is the reported core-hole lifetime for carbon 1s, $I_{isolated}$ is the integrated participator intensity for a long-lived reference, and $I_{coupled}$ is the participator intensity for a mixed monolayer. Here, in accordance with literature procedures, it was assumed that all aromatic carbon atoms were equally coupled to their surroundings and employed a PTCDI multilayer, for which the constituent molecules were poorly coupled to their surroundings, as the long-lived reference (FIG. 21). The calculations yielded charge transfer times of 11.5±1.5 fs for the P1 monolayer, 8.4±1 fs for the P2 monolayer, 5.2±0.5 fs for the P3 monolayer, and 5.7±0.6 fs for the P4 monolayer. Note that the errors were calculated by including the signal-to-noise ratio of the measured resonant spectra and the reported error of the C1s core-hole lifetime.

Figure 23:
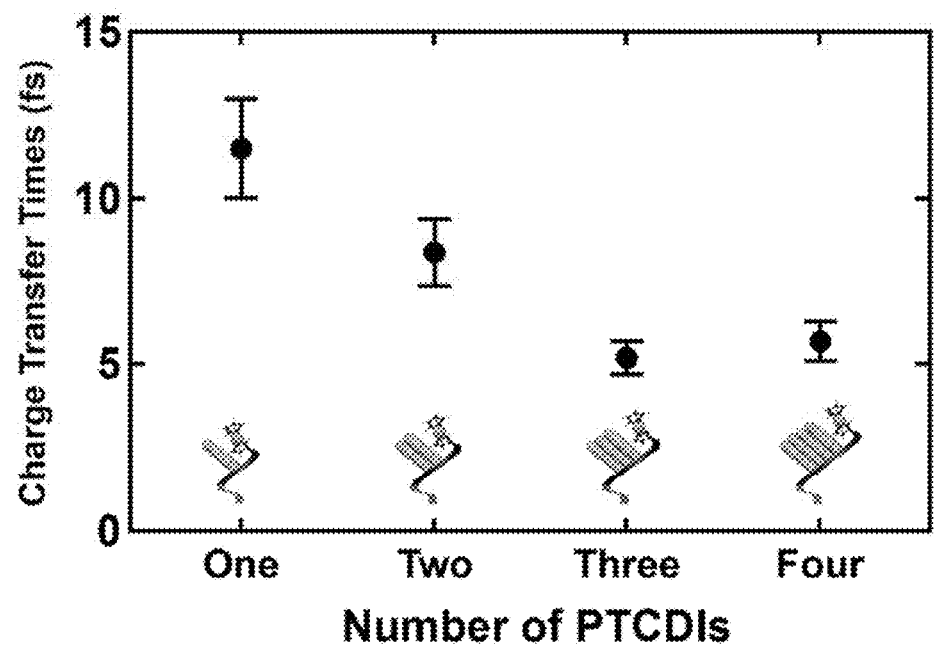
FIG. 23 provides graphs of the calculated charge transfer times for P1, P2, P3, and P4 and illustrations of the corresponding macromolecules are inset, generated in accordance with various embodiments of the invention, where the charge transfer times decrease as the length of the columnar molecular stack increases.
Figure 23:
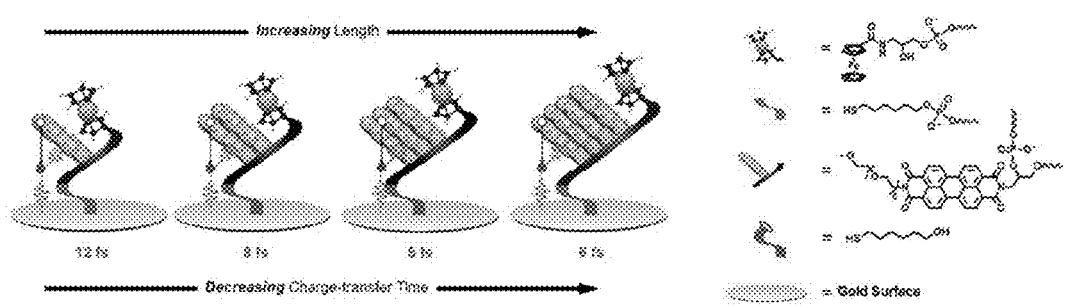

As demonstrated, the observed charge transfer times generally decreased with increasing molecular length (i.e. greater number of PDI building blocks), as shown in FIG. 23, with a substantial difference between monolayers from P1 and monolayers from P4. The observed trend is surprising, as previous studies have explicitly demonstrated that charge transfer times roughly increase with length for nitrile- and ferrocene-terminated alkanethiol monolayers (in contrast to our findings). Indeed, for the P1 to P4 series, the longer macromolecules extend farther from the surface and should be more poorly coupled with the substrate, hindering delocalization of the excited electrons and presumably leading to an increase (rather than a decrease) in the observed charge transfer times.

To rationalize our unexpected findings, the electronic structure of the P1 to P4 series were analyzed. For this purpose, molecular dynamics simulations may be used to obtain the equilibrium geometries of our macromolecules' PDI-based substructures and density functional theory calculations to generate the shapes and energies of their corresponding molecular orbitals. (See, e.g., T. Yanai, et al., Chem. Phys. Lett., 2004, 393, 51; and M. J. Frisch, et. al., Gaussian 09 (Revision D.01), Gaussian, Inc., Wallingford, CT, 2009, the disclosures of which are incorporated herein by reference.)

Figure 24:
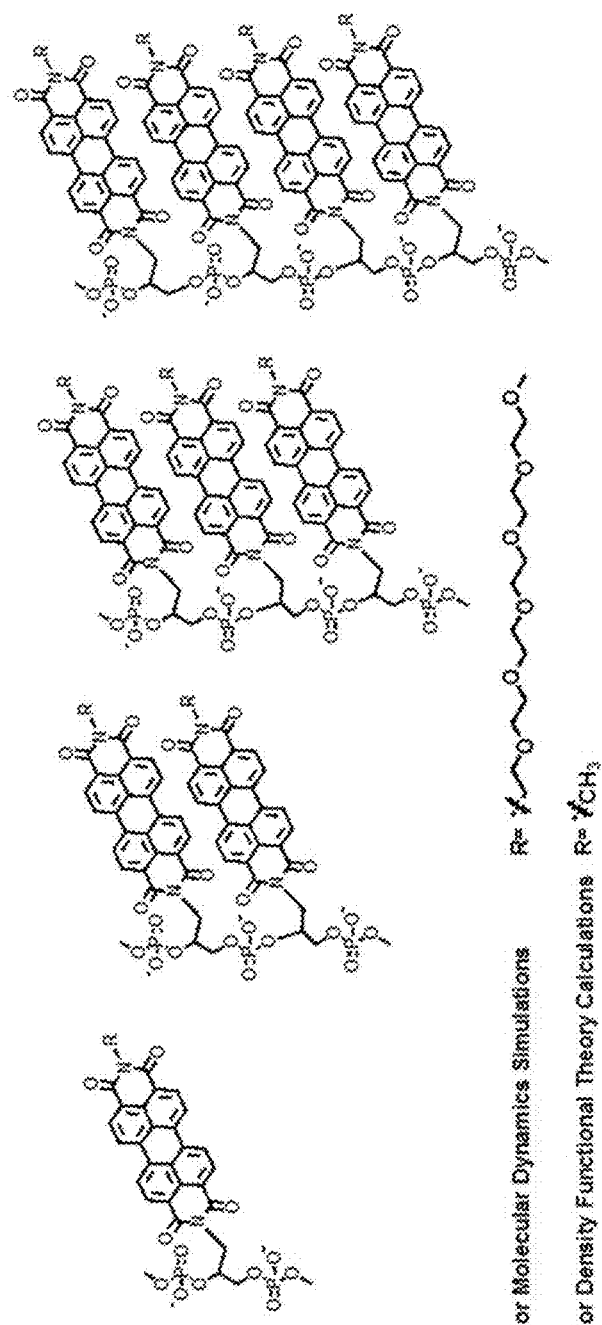
FIG. 24 provides molecular structure diagrams of the PDI subunits used for the molecular dynamics simulations, corresponding to macromolecules: P1, P2, P3, and P4, used in accordance with various embodiments of the invention.

Molecular Dynamics Simulations for the PDI-Based Macromolecules: The molecular dynamics simulations for macromolecules P1, P2, P3, and P4 were performed with GAFF in NAMD 2.9. The simulations employed the Generalized Born Implicit Solvent model (GBIS) and a monovalent salt concentration of 0.115 M. For the simulations, the subunits of P1, P2, P3, and P4 featuring the full-length side chains (FIG. 24) were parameterized according to established literature protocols and were in turn used for the molecular dynamics simulations. For each simulation, the starting configuration was obtained by turning off the attractive van der Waals interactions in the force field and setting the temperature to 500 K, thereby ensuring that all PDI moieties were completely separated from one another in an unstacked random open configuration. To initiate the simulation, the attractive van der Waals interactions were turned on, and the initial temperature was set to 300 K. All of the simulations were performed at a constant temperature of 300 K for 20 ns, ensuring that steady state was reached. The simulations were analyzed by monitoring the relative center of mass (COM) distances and offset angles for every pair of PDIs. The COM distances were calculated from the atomic coordinates and atomic mass of the individual PDIs. Here, the offset angles were obtained by constructing a vector from the nitrogen closest to the backbone to the nitrogen farthest from the backbone for the individual PDIs. The dot product of these vectors for every pair of PDIs defined the offset angles used for the analysis. The COM distances and offset angles indicated the relative separation and alignment of the PDIs, respectively, yielding the geometries in FIG. 25.

Ground state density functional theory calculations for the subunits of macromolecules P1, P2, P3, and P4 (FIG. 25) were performed in Gaussian 09. The averaged structures from the molecular dynamics simulations were used for the subunit geometries. For computational simplicity, the DFT calculations employed subunits that were substituted with methyl groups (rather than hexaethyleneglycol monomethyl ether) at the imide positions opposite to the phosphate backbone. The atomic orbitals were expanded in the cc-pVTZ and 6-31G(d,p) basis sets, and the ground state calculations were performed with all combinations of the aforementioned basis sets, as well as the CAM-B3LYP, B3LYP, and LC-wPBE functionals. The reported molecular orbitals for the LUMO+1 of the various macromolecules were observed for all combinations of functionals and basis sets. The results we report in the manuscript utilize the CAM-B3LYP functional and the cc-pVTZ basis set. The isosurface plots were rendered in VESTA. (See, e.g., M. J. Frisch, et al., Gaussian 09 (Revision D.01), Gaussian, Inc., Wallingford Conn., 2009; T. Yanai, et al., Chem. Phys. Lett., 2004, 393, 51; and K. Momma, F. Izumi, J. Appl. Crystallogr., 2011, 44, 1272, the disclosure of which are incorporated herein by reference.)

Interestingly, it is noted that the electron density was delocalized over either the entirety or majority of our macromolecules' aromatic cores, as exemplified by the isosurface plots of their LUMO+1 orbitals (See FIG. 19). In addition, it is found that P1, P2, P3, and P4 featured LUMO+1 energies of −0.9 eV, −2.9 eV, −3.2 eV, and −3.1 eV, respectively (note that these values are approximations, as the calculations employ functionals with limited accuracy and do not take into account solvent and substrate effects). Furthermore, in agreement with previous computational findings, it is observed that the appearance of multiple, distinct, energetically similar states for the macromolecules. (See, e.g., FIG. 19.) Given these calculations, the measured unexpected trend in the charge transfer times could be rationalized by considering the delocalization of the LUMO+1 orbitals, as well as the introduction of the new energy states, for P1, P2, P3, and P4. This length-dependent evolution in the macromolecules' electronic properties likely facilitated efficient delocalization of the excited electrons into their surroundings.

In conclusion, the excited-state charge transfer dynamics at PDI-based model organic-inorganic interfaces have been quantified, and the study holds significance for several reasons. First, the presented approach, in accordance with embodiments, employs entrenched DNA synthesis and self-assembly techniques to produce well defined arrays of columnar stacks of organic semiconductor building blocks at solid substrates. Such precise control is difficult to achieve within traditional synthesis and self-assembly contexts, potentially making this strategy valuable for understanding charge transfer phenomena. Second, the reported measurements reveal an unexpected trend in the rate of charge transfer from embodiments of macromolecules to their surroundings, which decreases, rather than increases, with molecular length. This trend can be rationalized by considering the evolution in electronic structure that occurs when organic semiconductors transition from isolated molecules to extended solids. Third, the experiments provide access to charge transfer dynamics at model interfaces with atomic-level chemical resolution and femtosecond-range temporal resolution. Given that core-level excited states share some common features with valence-level excited states for π-conjugated organic semiconductors, the strategy may prove valuable for fundamentally understanding interface-associated charge transfer dynamics across a broad range of carbon-based materials. Finally, the calculated charge transfer times of ~6 to ~12 fs measured for the DNA-like constructs are virtually identical to charge transfer times of ~6 fs measured for DNA under analogous conditions. This direct comparison is interesting from the perspective of the DNA conductivity field and supports the classic notion that duplex DNA shares characteristics with one-dimensional aromatic crystals, further underscoring the general applicability of the work. (See, e.g., L. Wang, et al. Appl. Phys. Lett., 2006, 89, 013902; H. S. Kato, et al., Phys. Rev. Lett., 2004, 93, 086403; J. C. Genereux, J. K. Barton, Chem. Rev., 2010, 110, 1642; N. B. Muren, et al., Phys. Chem. Chem. Phys., 2012, 14, 13754; and D. D. Eley, D. I. Spivey, Trans. Faraday Soc., 1962, 58, 411, the disclosure of which are incorporated herein by reference.)

Altogether, the methodology, according to embodiments, may open new opportunities for the fabrication of molecular wires, as well as the fundamental study of structure-function relationships in arbitrary organic materials, nanoscale charge transfer phenomena at device-relevant organic-inorganic interfaces, and conductivity in biological and bioinspired systems.

Example 4: Electrochemical Studies

Figure 26:
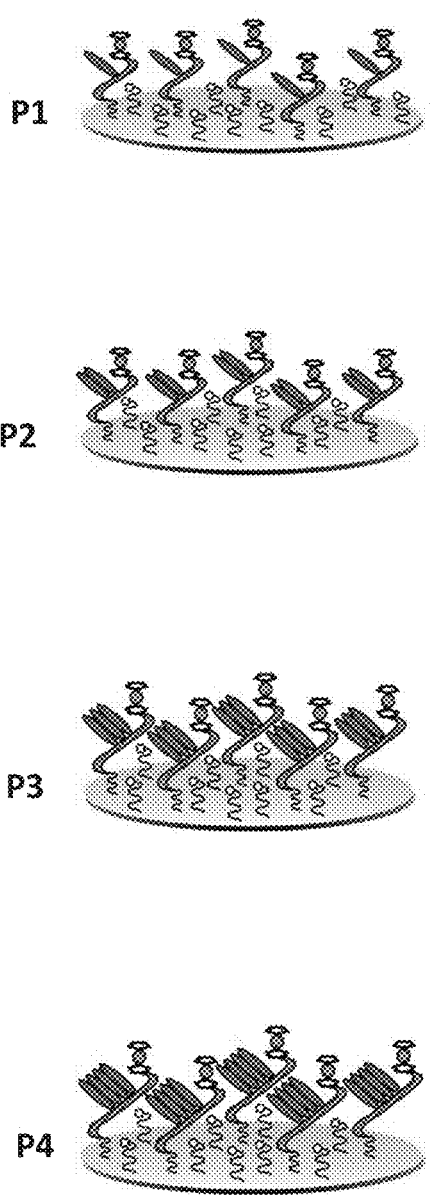
FIG. 26 provides schematic diagrams of a mercaptohexanol-backfilled monolayer from P1, P2, P3 and P4 (left column); and carbon K-edge NEXAFS spectra of the P1, P2, P3, and P4 monolayers measured with the electric field polarized parallel (red) and perpendicular (blue) to the gold surface, where the predicted theoretical spectrum for PTCDI is shown for comparison (dashed trace), where the substrate-relative orientation reported for the PTCDIs within the monolayer was calculated from the difference in signal intensity (dichroism) between the red and blue traces (right column), generated in accordance with various embodiments of the invention.
Figure 26:
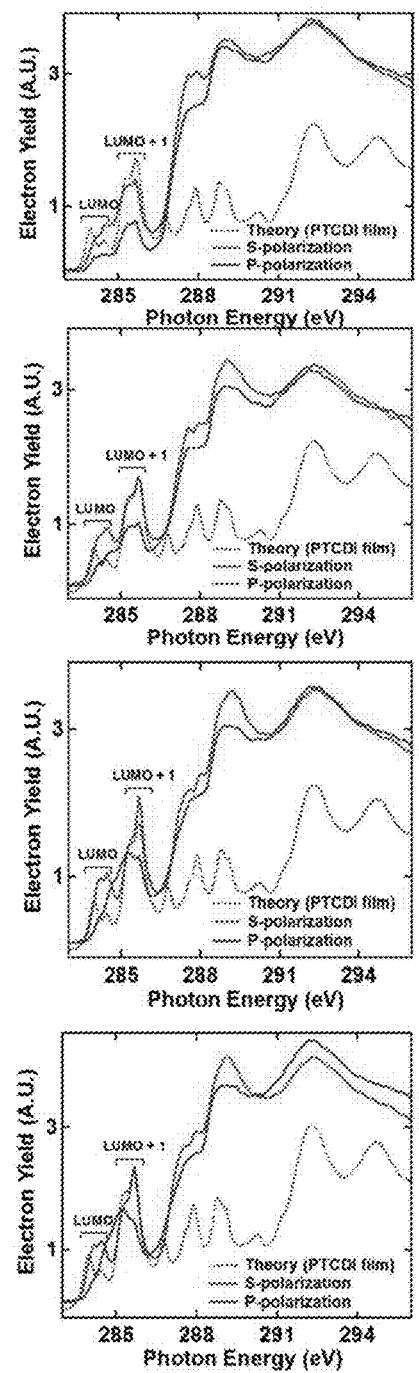

In another study, self-assembly and spectroscopic characterization of monolayers from P1, P2, P3, or P4 were prepared, as illustrated in FIG. 14. In the procedure, as described above, clean gold substrates were incubated with solutions of a plurality of thiol-modified constructs according to embodiments, allowing for formation of specific covalent S—Au bonds, and then the modified substrates were treated with mercaptohexanol to enforce an upright molecular wire orientation and displace non-specifically physisorbed species. In turn, the average orientation of the four monolayers' were confirmed to constituent macromolecules with near edge X-ray absorption fine structure spectroscopy (NEXAFS), which is a surface-sensitive technique that elucidates the electronic characteristics and orientation of surface-confined species. Thus, partial electron yield spectra were collected and analyzed with the incident electric fields parallel and perpendicular to the surface of our substrates (FIG. 26). Based on literature precedent for PDI-based materials, the spectras' were assigned characteristic inequivalent doublets at energies between 284 eV and 286 eV to carbon 1s→π* transitions that are associated with the LUMO (left doublet) and LUMO+1 (right doublet) orbitals, which are localized on the aromatic core of PDIs (FIG. 26). By evaluating the dependence of the LUMO+1 signals' intensity on the polarization of the electric field, we calculated average substrate-relative tilt angles of ~61±2°, ~61±2°, ~60±2°, or ~60±2° for the constituent PDIs of monolayers from P1, P2, P3, or P4, respectively. Overall, the NEXAFS experiments indicated that the macromolecules adopted nearly identical upright average orientations, in analogy to duplexes in backfilled DNA monolayers.

Figure 27A:
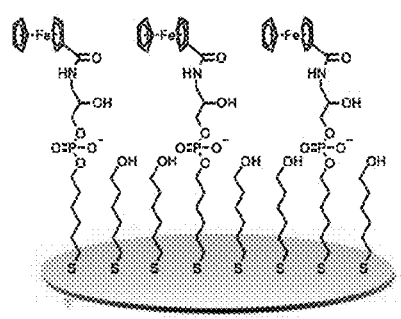
FIG. 27A provides a schematic diagram of a mercaptohexanol-backfilled monolayer from P0, generated in accordance with various embodiments of the invention.
Figure 27B:
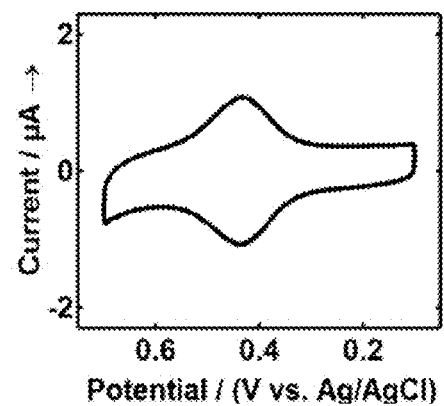
FIG. 27B provides a representative cyclic voltammogram obtained for a backfilled monolayer from P0, generated in accordance with various embodiments of the invention.
Figure 27C:
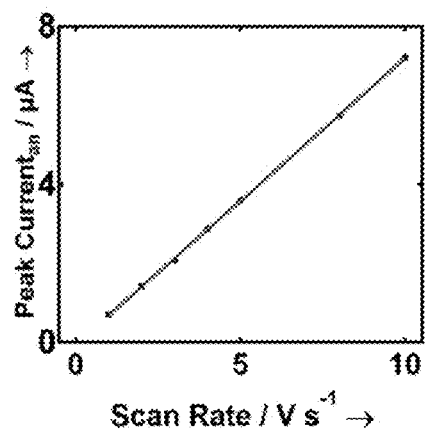
FIG. 27C provides a representative plot of the anodic peak current as a function of scan rate for a backfilled monolayer from P0, generated in accordance with various embodiments of the invention.

The electrochemical properties of backfilled monolayers from P0 were investigated, which is an analogue of the macromolecules but lacks any PDIs (FIG. 27A to d). Here, a redox couple at a potential of ~0.46 V (±0.002) mV vs. Ag/AgCl is observed, which can be attributed to the pendant ferrocene moiety (FIG. 27B). The couple featured an anodic to cathodic peak current ratio of 1.07 (±0.04), indicating a quasi-reversible redox reaction, and a linear dependence of the anodic peak current on the scan rate, indicating a surface bound species (FIG. 27C). From the anodic wave, a surface coverage of ~22 (±4) pmol/cm$^2$ is calculated, which was smaller than the estimated maximum coverages of ~300 and ~450 pmol/cm$^2$ for ferrocene-terminated DNA and alkanethiol monolayers, respectively, as well as a full width at half maximum (FWHM) of 0.14 (±0.004) V, which was greater than the ideal value of ~0.091 V. These metrics suggested a relatively dilute monolayer, likely due to repulsive electrostatic interactions between our constructs' negatively-charged backbones. Altogether, the measurements demonstrated that monolayers from P0 generally resembled analogous ones reported for ferrocene-terminated alkanethiols.

Figure 27D:
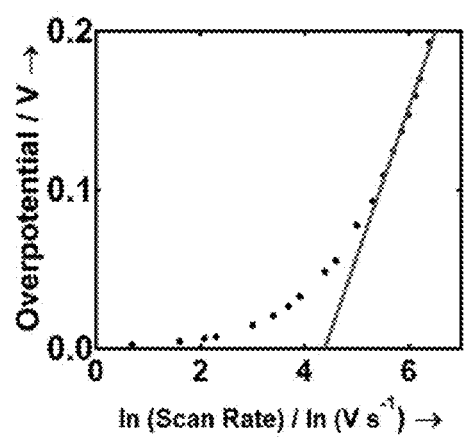
FIG. 27D provides a representative plot of the anodic overpotential as a function of the natural logarithm of the scan rate for P0, where the red line corresponds to the linear fit of the region with $\eta > 100$ mV, which is used to obtain the electron transfer coefficient $\alpha$ and the standard electron transfer rate constant $k_0$, generated in accordance with various embodiments of the invention.

Next the rate of electron transfer between the pendant ferrocene moieties and the gold electrode for P0 was evaluated, as mediated by the phospho-alkane bridge. By analyzing the cyclic voltammograms obtained at different scan rates, it was possible to extract the electron transfer rate constant $k_0$ according to the Laviron approach (FIG. 27D). The calculated $k_0$ for P0 was 9.7 (±1)×10$^2$ s$^{-1}$ (corresponding to a probe-electrode through-bond distance of 2.29 nm). This value was in good agreement with rate constants of $k_0$=6.0×10$^3$ $k_0$=1.2×10$^3$ s$^{-1}$, and $k_0$=1.0×10$^2$ s$^{-1}$ reported for analogous ferrocene-terminated alkanethiol monolayers, corresponding to probe-electrode through-bond distances of 1.84 nm, 2.00 nm, and 2.47 nm, respectively (See Table 1). These observations and analysis indicate that non-resonant tunneling was the likely mechanism governing electron transport through monolayers from P0.

TABLE 1

| Ferrocene | $k_0$ (s$^{-1}$) | Distance |
|---|---|---|
| FcCONH(CH$_2$)$_7$SH | 6.6 × 10$^4$ | 1.53 |
| FcCONH(CH$_2$)$_8$SH | 1.5 × 10$^4$ | 1.69 |
| FcCONH(CH$_2$)$_9$SH | 6.0 × 10$^3$ | 1.84 |
| FcCONH(CH$_2$)$_{10}$SH | 1.2 × 10$^3$ | 2.00 |
| FcCO$_2$(CH$_2$)$_{13}$SH | 1.0 × 10$^2$ | 2.47 |
| Fc(CH$_2$)$_{16}$SH | 2.8 × 10$^1$ | 2.65 |
| FcCONH(CH$_2$)$_{15}$SH | 7.0 × 10$^0$ | 2.77 |
| P0 | 9.7 (±1) × 10$^2$ | 2.29 |
| P1 | 8.2 (±1) × 10$^2$ | 3.05 |
| P2 | 8.3 (±0.8) × 10$^2$ | 3.81 |
| P3 | 8.8 (±1) × 10$^2$ | 4.57 |
| P4 | 8.2 (±0.8) × 10$^2$ | 5.33 |

[a] Electron transfer (ET) distance is defined as the sum of all the bond lengths between the pendant ferrocene and the terminal gold-bound sulphur atom.

Figure 28:
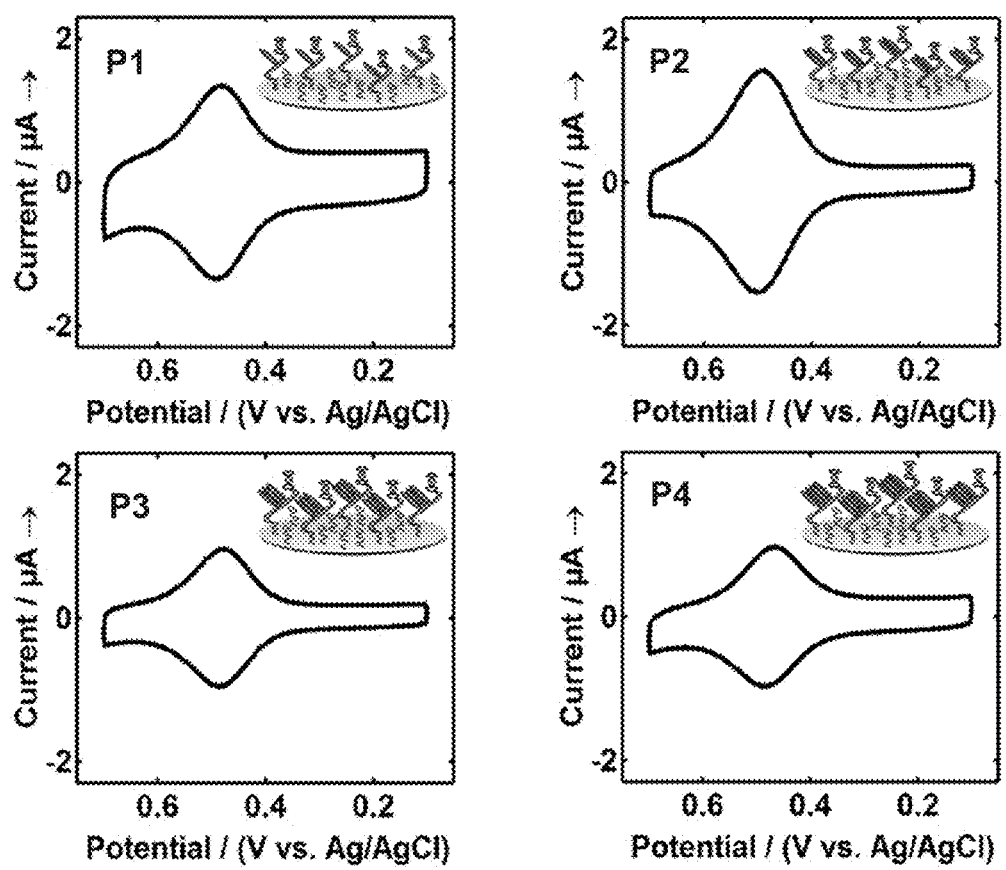
FIG. 28 provides representative cyclic voltammograms obtained for a backfilled monolayer from P1, P2, P3, and P4, where the insets are schematics of the corresponding monolayers, generated in accordance with various embodiments of the invention.
Figure 29:
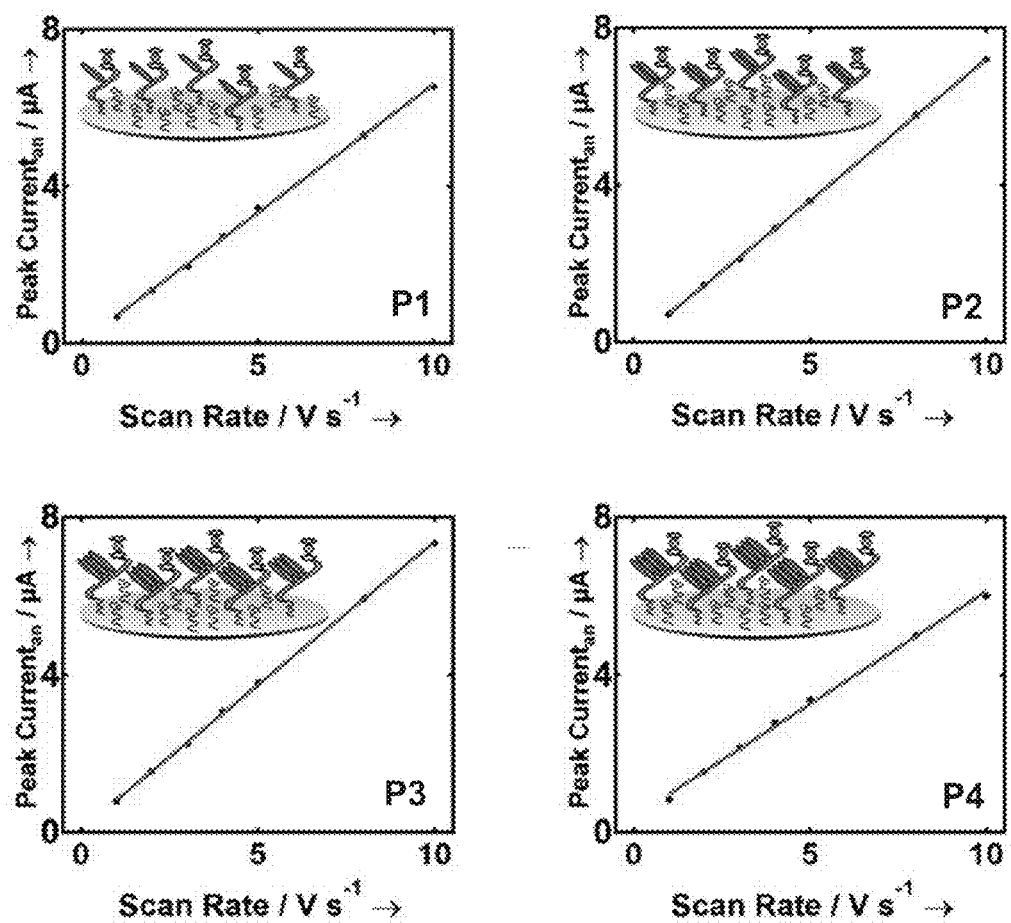
FIG. 29 provides the dependence of the anodic peak current on the scan rate for monolayers from P1, P2, P3, and P4, where the insets are schematics of the corresponding monolayers, generated in accordance with various embodiments of the invention.

The electrochemical properties of backfilled monolayers from P1, P2, P3, or P4 at positive potentials were also investigated (FIG. 28). These monolayers featured reversible redox couples at potentials of ~0.47 to ~0.52 V vs. Ag/AgCl, anodic to cathodic peak current ratios of ~1.02 to ~1.16, anodic FWHMs of ~0.13 V, average surface coverages of ~20 pmol/cm$^2$ to ~25 pmol/cm$^2$, and linear plots of peak current as a function of scan rate (FIG. 29 and Table 1). Altogether, measurements indicated that monolayers from P1, P2, P3, or P4 were relatively dilute and that their electrochemical characteristics closely resembled not only those of P0 but also one another.

Figure 30:
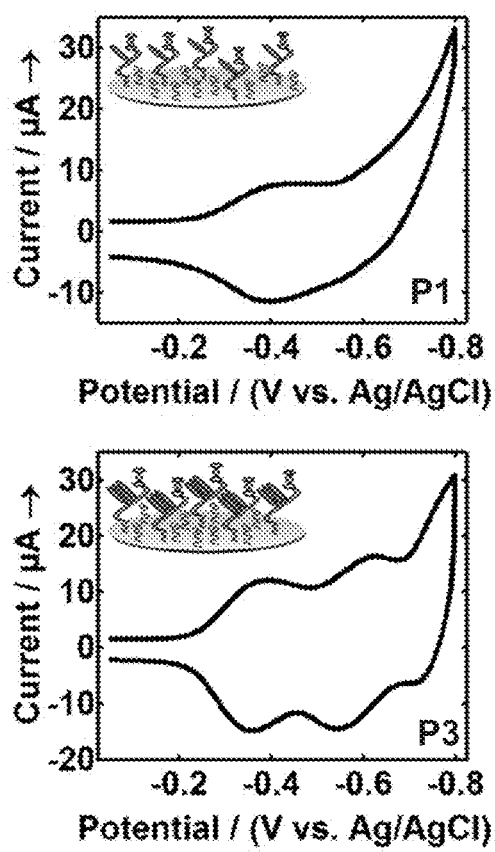
FIG. 30 provides cyclic voltammograms at negative potentials for mercaptohexanol-backfilled monolayers from P1, P2, P3, and P4, where the inserts show schematics of the corresponding molecular wires, generated in accordance with various embodiments of the invention.
Figure 30:
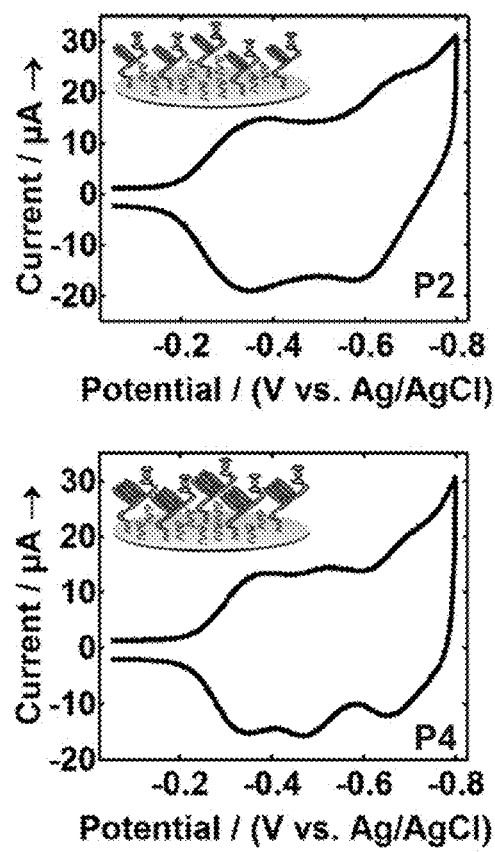
Figure 30:
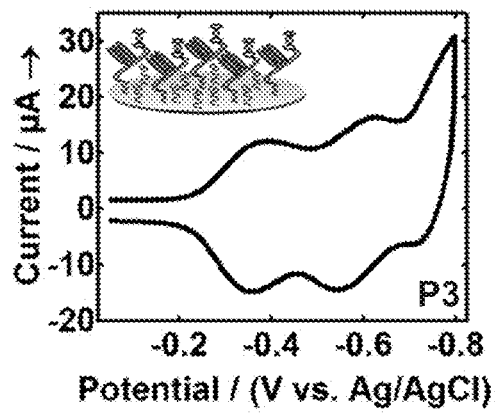
Figure 30:
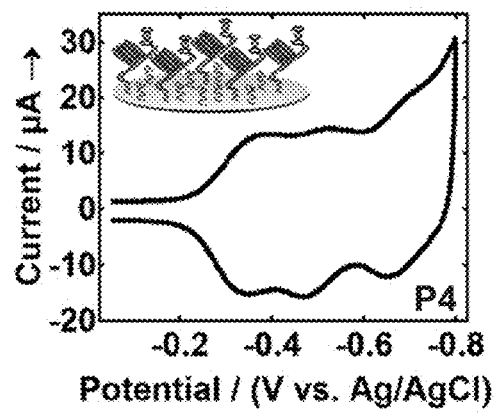

The electrochemical properties of backfilled monolayers from P1, P2, P3, or P4 at negative potentials were also investigated (FIG. 30). It was found that one to three quasi-reversible redox couples for P1, P2, P3, and P4, with a midpoint potential of ~−0.4 V vs. Ag/AgCl for the initial (least negative) couple in each instance. Based on literature precedent for PDIs, these redox signatures were attributed to the macromolecules' LUMOs (and energetically higher orbitals), and by using the pendant ferrocenes as internal standards, and reliable LUMO energies of −4.11 (±0.01) eV, −4.15 (±0.01) eV, −4.19 (±0.01) eV, and −4.22 (±0.01) eV for P1, P2, P3, and P4, were calculated, respectively. The lowering of the LUMO energies and appearance of multiple energetically similar states for the longer macromolecules indicated the likely presence of strong π-π stacking interactions between the constituent PDIs. Overall, the electrochemical measurements suggested that the PDI substructures essentially behaved as single electroactive units.

The rate of electron transfer through backfilled monolayers from P1, P2, P3, or P4 was also calculated. Here, the PDI-based substructures, along with their terminal linkers and tethers, served as extended bridges between the pendant ferrocenes and the gold surfaces. From an analysis of cyclic voltammograms obtained at different scan rates for the P1, P2, P3, and P4 monolayers, these macromolecules' respective electron transfer rate constants $k_0$ were extracted. The standard electron transfer rate constants $k_0$ for mercaptohexanol-backfilled monolayers from macromolecules P0, P1, P2, P3, and P4 were determined by following the Laviron approach for surface-bound redox-active species undergoing a reversible one-electron transfer process. For each of the monolayers, cyclic voltammograms were collected at scan rates between 1 and 4000 V s$^{-1}$, and the voltammograms that satisfied the criterion of kinetic overpotentials of $\eta=(E_p-E^{0'})>100$ mV were used for the calculations. In this limiting regime, the dependence of the overpotential on the natural logarithm of the scan rate ln(v) is given by the equations:

$$E_{pa} - E^{0'} = \left(\frac{RT}{(1-\alpha)nF}\right)\ln\left(\frac{(1-\alpha)nF}{RTk_f}\right) + \left(\frac{RT}{(1-\alpha)nF}\right)\ln v \text{ and} \quad (EQ. 2)$$

$$E_{pc} - E^{0'} = -\left(\frac{RT}{\alpha nF}\right)\ln\left(\frac{\alpha nF}{RTk_b}\right) - \left(\frac{RT}{\alpha nF}\right)\ln v \quad (EQ. 3)$$

where $E_{pa}$ is the potential of the anodic peak, $E_{pc}$ is the potential of the cathodic peak, v is the scan rate, α is the electron transfer coefficient, $k_f$ is the forward rate constant, $k_b$ is the backward rate constant, R is the ideal gas constant, T is the absolute temperature, F is the Faraday constant, and η is the number of electrons transferred. These equations were used to formulate plots of the overpotential η versus ln v, which featured linear regions for overpotentials η of >100 mV; as an example, a typical plot for P0 (including a fit of the linear regions) is shown in FIG. 27D. The electron transfer coefficients α were obtained from the slope of the fits to the linear regions. The electron transfer rate constants $k_0$ were obtained from the x-intercepts of the linear regions, which correspond to scan rates $v_a$ and $v_c$ where $\eta=0$ for the anodic and cathodic plots, respectively, and are defined by the equation:

$$k_0 = \frac{\alpha nFv_c}{RT} = \frac{(1-\alpha)nFv_a}{RT} \quad (EQ.\ 4)$$

The reported $k_0$ values correspond to an average of the electron transfer rate constants obtained from the anodic and cathodic plots, which exhibited minor differences (<50 s$^{-1}$).

Surprisingly for P1, only a small decrease in the electron transfer rate to $k_0=8.2\ (\pm 1)\times 10^2$ s$^{-1}$ was found, despite the greater probe-electrode through-bond distance of 3.05 nm, relative to P0 (Table 1). This value was in stark contrast to the slower rate constants of $k_0=2.8\times 10^1$ s$^{-1}$ and $k_0=7.0\times 10^0$ s$^{-1}$ found for ferrocene-terminated alkanethiols with probe-electrode through-bond distances of 2.65 nm and 2.77 nm, respectively (Table 1). Furthermore, it was discovered that the rate remained almost unchanged for the longer macromolecules, with values of $k_0=8.3\ (\pm 0.8)\times 10^2$ s$^{-1}$ for P2, $k_0=8.8\ (\pm 1)\times 10^2$ s$^{-1}$ for P3, and $k_0=8.2\ (\pm 0.8)\times 10^2$ s$^{-1}$ for P4, despite the substantially increased probe-electrode distances of 3.81 nm for P2, 4.57 nm for P3, and 5.33 nm for P4, respectively (Table 1). Together, the measurements indicated that the rate of electron transport through our molecular wires was effectively not attenuated with length.

Figure 25:
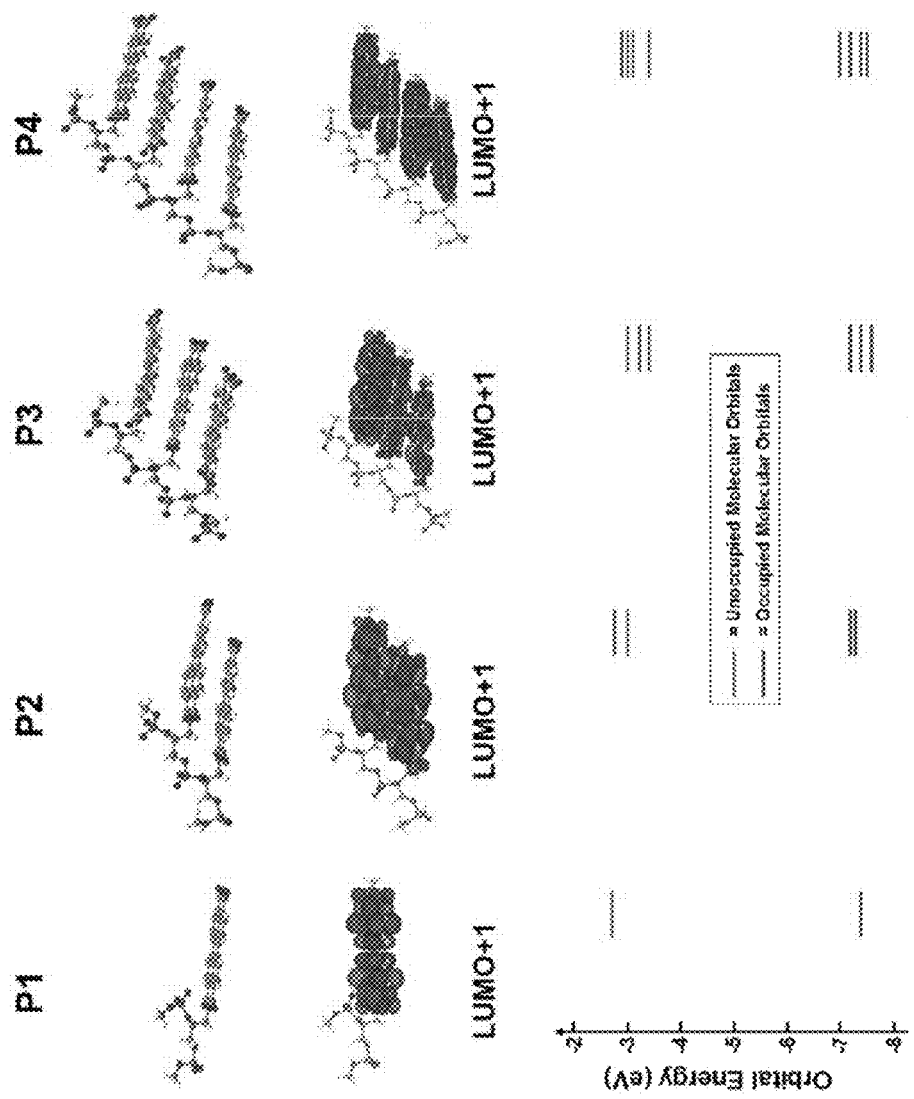
FIG. 25 provides equilibrium geometries of the PDI-containing subunits of P1, P2, P3, and P4 obtained from molecular dynamics simulations (top row); isosurface plots for the LUMO+1 of P1, P2, P3, and P4, where the isosurface values for all of the plots have been set to 0.01 |e|/Å$^3$ (middle row); and the theoretically determined energies of the LUMOs and HOMOs (as well as energetically-similar orbitals) for P1, P2, P3, and P4, generated in accordance with various embodiments of the current invention.

To facilitate interpretation of the experimental observations, DFT calculations were performed. Thus, molecular dynamics (MD) simulations were used to obtain the lowest free energy (most thermodynamically stable) atomistic conformations for the PDI-based substructures of P1, P2, P3, and P4 (FIGS. 13 and 25). The molecular dynamics simulations for the PDI-based substructures for molecular wires P1, P2, P3, and P4 were performed with GAFF in NAMD 2.9. The simulations employed the Generalized Born Implicit Solvent model (GBIS) and a monovalent salt concentration of 0.115 M. For the simulations, the substructures of P1, P2, P3, and P4 featuring the full length side chains were parameterized according to established literature protocols and were in turn used for the molecular dynamics simulations. For each simulation, the starting configuration was obtained by turning off the attractive van der Waals interactions in the force field and setting the temperature to 500 K, thereby ensuring that all PDI moieties were completely separated from one another in an unstacked random open configuration. To initiate the simulation, the attractive van der Waals interactions were turned on, and the initial temperature was set to 300 K. All of the simulations were performed at a constant temperature of 300 K for 20 ns, ensuring that steady state was reached. The simulations were analyzed by monitoring the relative center of mass (COM) distances and offset angles for every pair of PDIs. The COM distances were calculated from the atomic coordinates and atomic mass of the individual PDIs. Here, the offset angles were obtained by constructing a vector from the nitrogen closest to the backbone to the nitrogen farthest from the backbone for the individual PDIs. The dot product of these vectors for every pair of PDIs defined the offset angles used for the analysis. The COM distances and offset angles indicated the relative separation and alignment of the PDIs, respectively, yielding the geometries in FIG. 25.

The simulations revealed that the constituent PDIs of P2, P3, and P4 were offset with respect to one another but still featured strong π-π stacking interactions, in agreement with the characteristic changes observed for the constructs' UV-vis spectra. In turn, simulated equilibrium geometries and the long-range-corrected CAM-B3LYP functional were used to generate the shapes and energies of our four macromolecules' HOMOs and LUMOs. Ground state density functional theory calculations for the substructures of P1, P2, P3, and P4 were performed in Gaussian 09. The averaged structures from the molecular dynamics simulations were used for the substructure geometries. For computational simplicity, the DFT calculations employed PDIs that were substituted with methyl groups (rather than hexaethyleneglycol monomethyl ether) at the imide positions opposite to the phosphate backbone. The atomic orbitals were expanded in the cc-pVTZ and 6-31G(d,p) basis sets, and the ground state calculations were performed with all combinations of the aforementioned basis sets, as well as the CAM-B3LYP, B3LYP, and LC-wPBE functionals. The results reported utilize the CAM-B3LYP functional and the cc-pVTZ basis set. The molecular orbitals were obtained in Gaussian 09 for the HOMO and LUMO of each PDI-based macromolecule. The isosurface plots were rendered in VESTA.

The isosurface plots revealed that the electron density was delocalized over either the entirety or majority of the substructures' aromatic cores, demonstrating that the constituent PDI moieties were not electronically independent of one another (FIG. 25). Moreover, the theoretically-predicted LUMO energies were lowered for the longer macromolecules, with values of −2.66 eV, −3.01 eV, −3.36 eV, and −3.36 eV for P1, P2, P3, and P4 respectively, in agreement with the trend found during the electrochemical measurements (note that the theoretical and experimental values do not perfectly match due to the limited accuracy of the functional and the exclusion of solvent and/or substrate effects). Overall, the calculations shed insight into the electronic structure of our constructs and provided a rationale for their electrochemical behavior as single electroactive units.

The experimental observations warrant a discussion of the likely mechanism governing electron transport for P1, P2, P3, and P4. Here, it is noted that constructs according to embodiments consist of several distinct components: π-conjugated PDI-based substructures, primarily saturated tethers bound to the electrodes, and primarily saturated linkers to the pendant ferrocene probes. Based on previous findings for ferrocene-terminated alkanethiols (as well as on experimental observations for monolayers from P0), electrons are likely transported through the macromolecules' tethers and linkers via a rate-limiting and loosely non-resonant tunneling mechanism. Furthermore, based on reports of rapid electron hopping rates of >10$^7$ s$^{-1}$ and femtosecond charge transfer times in analogous PDI-based ensembles, (as well as our computational observations for P1, P2, P3, and P4), electrons are likely transported through the macromolecules' PDI-based substructures via a rapid and nearly lossless resonant tunneling mechanism. The combination of these two mechanisms accounts for the observation of essentially length-independent charge transport for embodiments of the constructs.

Figure 31:
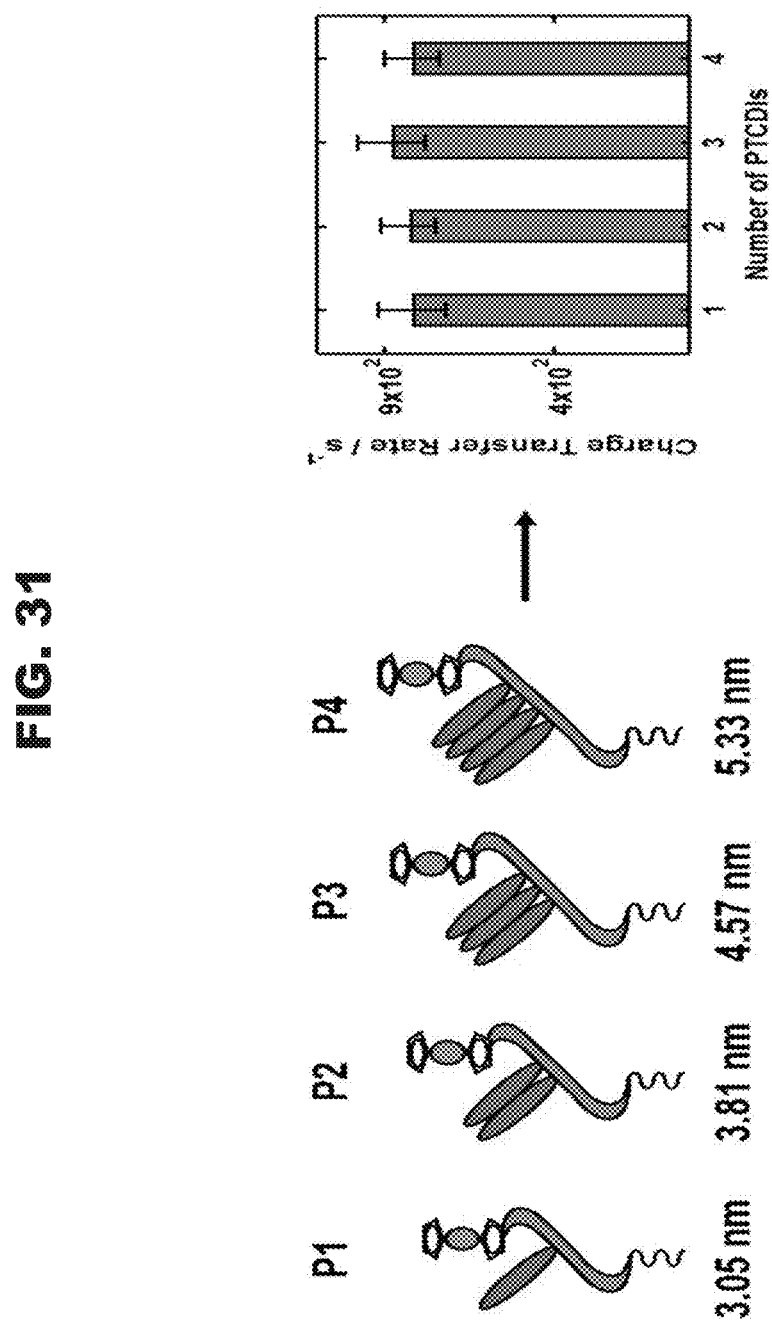
FIG. 31 provides plots of the rate of electron transport through exemplary wires, generated in accordance with various embodiments of the invention, showing that they are essentially independent of their length.

In summary, embodiments provide a series of polymeric PDI chimeric molecular wires having unique charge transport properties. These studies hold significance for several reasons. First, the reported synthetic methodology employs straightforward, readily accessible bioconjugate chemistry techniques to prepare well-defined PDI-based polymer macromolecules. In principle, this approach possesses few limitations and could be used to prepare a variety of modular, sequence-variable constructs from arbitrary organic semiconductor building blocks. Second, the electrochemical strategy makes it possible to simultaneously measure charge transport rates and monitor changes in electronic structure. Such experimental flexibility underscores the value of the methodology for the study of nanoscale charge transport phenomena. Finally, the measurements reveal that the rate of electron transport through embodiments of molecular wires is not attenuated with length, as is summarized in FIG. 31. The reported constructs may thus prove valuable as archetypes for the construction of novel high-performance electronic components. Altogether, the findings hold broad relevance within the context of carbon-based molecular, organic, and biological electronics and may afford new opportunities for the development of advanced miniaturized circuits.

DOCTRINE OF EQUIVALENTS

As can be inferred from the above discussion, the above-mentioned concepts can be implemented in a variety of arrangements in accordance with embodiments of the invention. Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:
1. An engineered perylene diimide polymer having a phosphate backbone comprising:

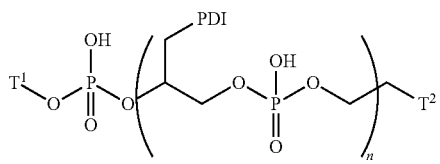

wherein T1 and T2 are termini;
wherein n is a positive integer; and
wherein PDI is a perylene diimide comprising:

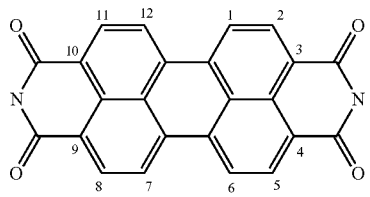

wherein N is an imide, and wherein a first imide is covalently linked to the phosphate backbone, and wherein a second imide is functionalized with a substituent selected from the group consisting of H, alkyl, aryl, polyethylene glycol, Newkome-type carboxylates, phosphate surfactants, polyglycerol dendrons, and clycodextrin; and
wherein positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups.

2. The perylene diimide polymer of claim 1, wherein the polymer is engineered to a precise length and sequence such that a collection of polymers is monodisperse.

3. The perylene diimide polymer of claim 1, wherein n is equal to four.

4. The perylene diimide polymer having a phosphate backbone of claim 1, wherein n is greater than 20.

5. The perylene diimide polymer of claim 1, wherein n is greater than 100.

6. The perylene diimide polymer of claim 1, wherein at least two perylene diimides, each having a different chemical structure, are incorporated into the polymer.

7. The perylene diimide polymer of claim 1, wherein the polymer has an engineered sequence of perylene diimides.

8. The perylene diimide polymer of claim 1, wherein at least one perylene diimide is functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

9. The perylene diimide polymer of claim 1, wherein at least one perylene diimide is functionalized on a second imide with polyethylene glycol.

10. The perylene diimide polymer of claim 1, wherein at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

11. The perylene diimide polymer of claim 1, wherein at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.

12. The perylene diimide polymer of claim 1, wherein at least two perylene diimides are functionalized on a second imide with polyethylene glycol.

13. The perylene diimide polymer of claim 1, wherein T1 and T2 are each independently selected from the group consisting of an amino group, a hydroxyl group, a carbonyl group, ferrocene and thiol.

14. A method of forming a perylene diimide polymer having a phosphate backbone of claim 1 comprising:
providing a plurality of perylene diimides comprising:

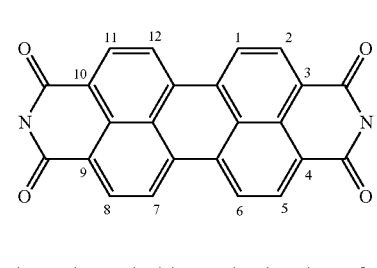

wherein N is an imide, and wherein a first imide is covalently linked to a phosphate functionality;
wherein a second imide is functionalized with a substituent selected from the group consisting of H, alkyl, aryl, polyethylene glycol, Newkome-type carboxylates, phosphate surfactants, polyglycerol dendrons, and clycodextrin; and wherein positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups;

iteratively and sequentially linking a plurality of the perylene diimides through via the phosphate functionality to form the phosphate backbone through a nucleoside polymerization protocol such that a specific arrangement and number, n, of perylene diimides is obtained; and selectively terminating the polymer with termini T1 and T2.

15. The method of claim 14, wherein n is equal to four.
16. The method of claim 14, wherein n is greater than 20.
17. The method of claim 14, wherein n is greater than 100.
18. The method of claim 14, wherein the phosphate is a phosphoramidite.
19. The method of claim 14, wherein at least two perylene diimides, each having a different chemical structure, are incorporated into the polymer.
20. The method of claim 14, wherein at least one perylene diimide is functionalized on a position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
21. The method of claim 14, wherein at least one perylene diimide is functionalized on a second imide with polyethylene glycol.
22. The method of claim 14, wherein at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
23. The method of claim 14, wherein at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
24. The method of claim 14, wherein at least two perylene diimides are functionalized on a second imide with polyethylene glycol.
25. The method of claim 14, wherein T1 and T2 are each independently selected from the group consisting of an amino group, a hydroxyl group, a carbonyl group, ferrocene and thiol.
26. An organic nanowire comprising:
a perylene diimide polymer having a phosphate backbone comprising:

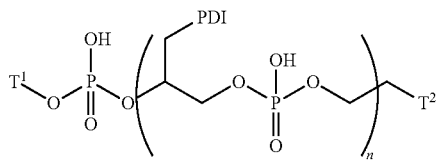

wherein T1 and T2 are termini;
wherein n is a positive integer; and
wherein PDI is a perylene diimide comprising:

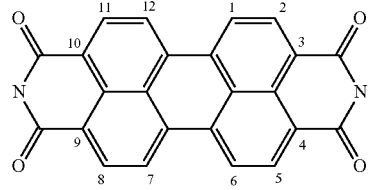

wherein N is an imide, and wherein a first imide is covalently linked to the phosphate backbone;
wherein a second imide is functionalized with a substituent selected from the group consisting of H, alkyl, aryl, polyethylene glycol, Newkome-type carboxylates, phosphate surfactants, polyglycerol dendrons, and clycodextrin; and
wherein positions 1, 2, 5, 6, 7, 8, 11, and 12 are functionalized with a substituent selected from the group consisting of H, F, Cl, Br, CN, alkyl group, aryl group, aryloxy group, polyethylene glycol, and electron-withdrawing/donating groups.

27. The organic nanowire of claim 26, wherein the polymer is engineered to a precise length and sequence such that a collection of polymers is monodisperse.
28. The organic nanowire of claim 26, wherein at least two perylene diimides, each having a different chemical structure, are incorporated into the polymer.
29. The organic nanowire of claim 26, wherein at least one perylene diimide is functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
30. The organic nanowire of claim 26, wherein at least one perylene diimide is functionalized on at least two positions selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
31. The organic nanowire of claim 26, wherein at least two perylene diimides are functionalized on at least one position selected from the group of positions 1, 2, 5, 6, 7, 8, 11, and 12 with a substituent selected from the group consisting of F, Cl, Br, CN, alkyl group, aryl group, aryloxy group, polyethylene glycol, and electron-withdrawing/donating groups.
32. The organic nanowire of claim 26, wherein T1 and T2 are each independently selected from the group consisting of an amino group, a hydroxyl group, a carbonyl group, ferrocene and thiol.
33. The organic nanowire of claim 26, wherein the organic nanowire is incorporated into an electronic device.
34. The organic nanowire of claim 33, wherein the electronic device is an organic field-effect transistor.

* * * * *

UNITED STATES PATENT AND TRADEMARK OFFICE
CERTIFICATE OF CORRECTION

Page 1 of 1

PATENT NO. : 10,017,528 B2
APPLICATION NO. : 15/707851
DATED : July 10, 2018
INVENTOR(S) : Amir Mazaheripour, Anthony Burke and Alon Gorodetsky It is certified that error appears in the above-identified patent and that said Letters Patent is hereby corrected as shown below:

In the Specification

Column 1, Line 12, insert the following paragraph:
--STATEMENT REGARDING FEDERALLY SPONSORED RESEARCH
This invention was made with Government support under Grant No. FA9550-13-1-0096, awarded by the AFSOR. The Government has certain rights to this invention.--

Signed and Sealed this
Sixth Day of December, 2022

Katherine Kelly Vidal
*Director of the United States Patent and Trademark Office*